US010203272B2

(12) United States Patent
Wilson et al.

(10) Patent No.: US 10,203,272 B2
(45) Date of Patent: Feb. 12, 2019

(54) MEMS AEROSOL IMPACTOR

(71) Applicant: Colorado Seminary, which owns and operates the University of Denver, Denver, CO (US)

(72) Inventors: James C. Wilson, Golden, CO (US); Siavash Pourkamali Anaraki, Dallas, TX (US)

(73) Assignee: Colorado Seminary, University of Denver, Denver, CO (US)

( * ) Notice: Subject to any disclaimer, the term of this patent is extended or adjusted under 35 U.S.C. 154(b) by 592 days.

(21) Appl. No.: 14/777,374

(22) PCT Filed: Mar. 14, 2014

(86) PCT No.: PCT/US2014/029280
§ 371 (c)(1),
(2) Date: Sep. 15, 2015

(87) PCT Pub. No.: WO2014/153142
PCT Pub. Date: Sep. 25, 2014

(65) Prior Publication Data
US 2016/0047728 A1 Feb. 18, 2016

Related U.S. Application Data

(63) Continuation-in-part of application No. PCT/US2011/055911, filed on Oct. 12, 2011.
(Continued)

(51) Int. Cl.
*G01N 15/02* (2006.01)
*G01H 11/08* (2006.01)
(Continued)

(52) U.S. Cl.
CPC ......... *G01N 15/0255* (2013.01); *G01H 11/08* (2013.01); *G01N 1/22* (2013.01);
(Continued)

(58) Field of Classification Search
CPC ...... G01N 15/0255; G01N 1/22; G01N 15/06; G01N 2015/0046; G01N 2015/0261; G01H 11/08
(Continued)

(56) References Cited

U.S. PATENT DOCUMENTS

| 3,488,530 A | 1/1970 | Staudte |
| 3,653,253 A | 4/1972 | Olin |

(Continued)

FOREIGN PATENT DOCUMENTS

WO 2012051256 A1 4/2012

OTHER PUBLICATIONS

International Preliminary Report on Patentability dated Mar. 14, 2013 in application No. PCT/US2014/029280.
(Continued)

*Primary Examiner* — Daniel S Larkin
(74) *Attorney, Agent, or Firm* — Maschoff Brennan

(57) ABSTRACT

Embodiments of the invention include aerosol impactors comprising one or more micromechanical resonators. Impactors according to embodiments of the invention can provide size classification and/or concentration of aerosol particulate. Aerosol impactors can use an air flow device, such as a pump, to create a constant flow of air. Nozzles of varying diameters are used to separate particulate of varying sizes and the particles that pass through strike a measuring device. MEMS resonators can be integrated into arrays to provide mass sensitivity in a small, lightweight and cost effective package, which will effectively allow for the measurement of the mass of every micro/nanoscale particle landing on the surface.

18 Claims, 33 Drawing Sheets

Related U.S. Application Data

(60) Provisional application No. 61/784,926, filed on Mar. 14, 2013.

(51) Int. Cl.
*G01N 15/06* (2006.01)
*G01N 1/22* (2006.01)
*G01N 15/00* (2006.01)

(52) U.S. Cl.
CPC ..... *G01N 15/06* (2013.01); *G01N 2015/0046* (2013.01); *G01N 2015/0261* (2013.01)

(58) Field of Classification Search
USPC .......................................................... 73/24.03
See application file for complete search history.

(56) References Cited

U.S. PATENT DOCUMENTS

| | | | |
|---|---|---|---|
| 3,854,321 A | 12/1974 | Dahneke | |
| 4,041,768 A | 8/1977 | Gilbert et al. | |
| 5,020,370 A | 6/1991 | Deval et al. | |
| 5,128,539 A | 7/1992 | Rodgers et al. | |
| 5,825,119 A * | 10/1998 | Shibata | B06B 1/0644 310/324 |
| 6,190,035 B1 | 2/2001 | Smith | |
| 6,431,014 B1 | 8/2002 | Liu et al. | |
| 6,786,075 B2 | 9/2004 | Radke et al. | |
| 6,930,569 B2 | 8/2005 | Hsu | |
| 6,972,841 B2 | 12/2005 | Krempl et al. | |
| 6,990,846 B2 | 1/2006 | Sioutas | |
| 7,140,266 B2 | 11/2006 | Marjamaki et al. | |
| 7,146,857 B2 | 12/2006 | Hök | |
| 7,318,338 B2 | 1/2008 | Moisio et al. | |
| 7,586,239 B1 | 9/2009 | Li et al. | |
| 8,230,724 B2 | 7/2012 | Gehring | |
| 8,256,298 B2 | 9/2012 | Suijlen et al. | |
| 2006/0290449 A1 | 12/2006 | Piazza et al. | |
| 2008/0297281 A1 | 12/2008 | Ayazi et al. | |
| 2009/0249873 A1 | 10/2009 | Delevoye | |
| 2010/0186524 A1 | 7/2010 | Ariessohn et al. | |
| 2011/0290002 A1 | 12/2011 | Heidrich et al. | |

OTHER PUBLICATIONS

Written Opinion dated Jul. 29, 2014 as received in Application No. PCT/US2014/029280.
Search Report dated Jul. 29, 2014 as received in Application No. PCT/US2014/029280.
Search Report dated Mar. 23, 2012 as received in Application No. PCT/US2011/055911.

* cited by examiner

MEMS AEROSOL IMPACTOR

CROSS-REFERENCES TO RELATED APPLICATIONS

This application is a continuation-in-part of and claims the benefit of PCT Patent Application PCT/US11/55911, which was filed Oct. 12, 2011, the complete disclosure of which is herein incorporated by reference.

GOVERNMENT RIGHTS CLAUSE

This invention was made with government support under National Science Foundation Grant Number 0800961. The government has certain rights in the invention.

BACKGROUND

Aerosol impactors are used in industrial or scientific applications to monitor the concentration of airborne particulate. Airborne particles play important roles in air quality, human health, visibility in the atmosphere, the radiation balance of the earth, and stratospheric ozone depletion.

BRIEF SUMMARY

Embodiments of the invention include aerosol impactors comprising one or more micromechanical resonators. Impactors according to embodiments of the invention can provide size classification and/or concentration of aerosol particulate. Aerosol impactors can use an air flow device, such as a pump, to create a constant flow of air. Nozzles of varying diameters are used to separate particulate of varying sizes and the particles that pass through or strike a measuring device. Microelectromechanical systems or micromechanical (MEMS) resonators can be integrated into arrays to provide mass sensitivity in a small, lightweight and cost effective package, which will effectively allow for the measurement of the mass of every micro/nanoscale particle landing on the surface.

These resonators can be fabricated, for example, from thin silicon layers. Both rotational and translational mode resonators are disclosed. Translational resonators can include two plates coupled by two or more actuator beams. A stable DC bias current can be applied across the actuator beams to cause the plates to resonate. In other embodiments, disk resonators can be used in a rotational mode. The mass of aerosol particles on the resonator may be measured by monitoring the resonance frequency of the resonator.

In one aspect, the present invention provides a particle impactor. The particle impactor can include a housing and a nozzle disposed within the housing that includes an aperture to allow for the passage of air through the housing. The particle impactor can further include MEMS resonator positioned within the housing near the nozzle to capture particles within the air flowing through the housing. The particles can be within a predetermined size group, and the MEMS resonator can have a resonant frequency that shifts when a particle impacts a portion of the resonator. In some embodiments, the MEMS resonator is one of a plurality of MEMS resonators disposed on an impactor surface positioned below the nozzle. The particle impactor can be powered by a battery. In some cases, the MEMS resonator is less than or equal to 400 $\mu m^2$ in area. In other cases, the MEMS resonator is less than or equal to 10 $\mu m^2$ in area. In one embodiment, the particle impactor has a volume less than or equal to 40 $cm^3$. In other embodiments, the particle impactor has a volume less than or equal to 10 $cm^3$.

In some embodiments, the nozzle is one of a plurality of nozzles and the MEMS resonator is one of a plurality of MEMS resonators. Each nozzle is aligned with a corresponding MEMS resonator. Each successive nozzle is configured to allow particles with different predetermined size groups to flow through the housing. Each successive MEMS resonator is configured to be sensitive to frequency shifts to detect the presence of different sized particles. In some embodiments, the MEMS resonator includes two masses coupled with at least one beam, and two pads electrically coupled with the beam. The masses resonate with a fixed frequency when a constant current runs through the beam. The MEMS resonator further includes a second beam coupled with each of the two masses. In some cases, the MEMS resonator includes doped silicon. The MEMS resonator can be connected to an electrical bus, a processor, and a memory device, where the processor is configured to convert frequency shifts to particle mass or particle concentration data. The processor can be configured to indicate mass or particle concentration data in real-time.

In another aspect, the present invention provides a method for measuring particulate concentration. The method can include flowing air through a housing and filtering aerosol particles within the air. A frequency shift of a MEMS resonator as the aerosol particles impact the MEMS resonator can be measured. The method can also include determining the mass or concentration of aerosol particles in a size group using the frequency shift. The method can further include indicating particulate mass or concentration levels in real-time. The measuring can be done using an array of MEMS resonators.

In one aspect, the present invention provides a particle impactor. The particle impactor can include a housing having a volume less than or equal to 10 $cm^3$ and a nozzle disposed within the housing. The nozzle can include a plurality of micromachined apertures to allow for the passage of air through the housing. The particle impactor can further include a thermo-piezoresistive micromachined resonator positioned within the housing near the nozzle to capture particles within the air flowing through the housing. The particles can be within a predetermined size group. The thermo-piezoresistive micromachined resonator can have an area less than or equal to 100 $\mu m^2$. The thermo-piezoresistive micromachined resonator can have a resonant frequency that shifts when a particle impacts a portion of the thermo-piezoresistive micromachined resonator.

In some embodiments, the thermo-piezoresistive micromachined resonator includes a plurality of isolated ground connections configured to generate an electrodynamic particle sweep. The nozzle can be one of a plurality of nozzles and the thermo-piezoresistive micromachined resonator can be one of a plurality of thermo-piezoresistive micromachined resonators. Each nozzle can be aligned with a corresponding thermo-piezoresistive micromachined resonator. The plurality of micromachined apertures of each successive nozzle can be configured to allow particles with different predetermined size groups to flow through the housing. Each successive thermo-piezoresistive micromachined resonator is configured to be sensitive to frequency shifts to detect the presence of different sized particles. The thermo-piezoresistive micromachined resonator can be one of a plurality of thermo-piezoresistive micromachined resonators disposed on an impactor surface positioned below the nozzle.

Terms such as "invention" or "the invention" or "this invention" or "the present invention" and the like as used in this patent are intended to refer broadly to all of the subject matter of this disclosure and the claims below. Statements containing these terms should not be understood to limit the subject matter described herein or to limit the meaning or scope of the claims below. Embodiments of the invention are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to the entire specification of this patent, all drawings and each claim.

BRIEF DESCRIPTION OF THE DRAWINGS

Illustrative embodiments of the present invention are described in detail below with reference to the following drawing figures.

Embodiments of the invention are directed toward an aerosol impactor utilizing MEMS resonators (e.g., a micromachined thermo-piezoresistive resonator (TPR)). In some embodiments, a number of MEMS resonators can be used in a cascade aerosol impactor. TPRs are electronically actuated using electro-thermal forces and their mechanical vibration frequency can be monitored using the output signal generated by the piezoresistive effect. TPRs can be fabricated using a micromachining process including a lithography step. Some TPRs can be very small and require minimal electronic circuitry for operation. TPRs can initiate and maintain self-oscillation without the need for any external electronic amplification and, therefore, may only require only simple digital circuitry to measure and record the deposited mass on them.

Embodiments of the invention have real-world applicability. Due to the ability of fabricating MEMS resonators of a very small size at a low cost per unit, an entire MEMS aerosol impactor can be constructed in a portable, wearable package, allowing aerosol particulate concentration levels to be measured in real-time for a variety of applications. For example, measuring particulate in lab air, in mining applications, and general air quality would all benefit from access to small, affordable MEMS aerosol impactors.

This description begins by describing various embodiments of MEMS resonators and is followed by a discussion on cascade impactors, generally. Following this, integration of MEMS resonators into such impactors is disclosed.

Embodiments of the invention include various micromechanical resonators. Such resonators typically have dimensions less than or equal to about 500 μm. These resonators can have either translational or rotational modes. In some embodiments, two micromechanical plates can be coupled with one or more beams. A constant current can be applied to the resonator through the beams, which starts a cycle of heating and cooling of the beams that result in a corresponding stress and therefore cycle of changes in the resistance of the beams. This change can result in a change in voltage measured across the beams. These cycles can reach resonance producing a constant frequency response with some temperature related drift. Disk resonators can include a disk coupled with two actuating beams. When an actuation current is applied, which may include both a DC and AC component, the disk rotates back and forth with a small amplitude and the beams expand and contract in a manner similar to the beams in translational mode resonators producing regular oscillations.

FIG. 1 shows an in-plane resonator according to some embodiments of the invention. Resonator 100 can include plate 105 and plate 106 that are coupled together via beam 110 and beam 111. Resonator 100 can be a monolithic and/or unitary structure. That is, beam 110, beam 111, plate 105, and plate 106 can be constructed from the same material during the same process. In some embodiments, resonator 100 can be etched from a substrate; for example, a substrate with silicon, doped silicon, N-type silicon, P-type silicon, silicon oxide, silicon carbide, germanium, etc. Resonator 100 can be made from any type of conductor or semiconductor material. Resonator 100 can be released from the substrate using any number of undercut methods; for example, using hydrofluoric acid. In some embodiments, beam 110 and/or beam 111 can be thinned down by various post etching techniques such as thermal oxidation and subsequent oxide removal.

Plates 105 and plate 106 can be masses that oscillate relative to one another while beams 110 and 111 expand and contract. That is, plate 105 and plate 106 can move back and forth in opposite directions causing beam 110 and beam 111 to compress and expand periodically when a DC bias current is applied. In some embodiments, the DC bias current can be applied between beam 110 and beam 111, for example, at or near the center of beam 110 and beam 111 (e.g., as shown in FIG. 4). In other embodiments, the DC bias current can be applied between plate 105 and plate 106. Beam 110 and beam 111 can act as thermal actuators and/or piezoresistive sensors.

Support beams 120 on the outer corners of plates 105 and 106 can be included to add vertical stiffness to plates 105 and 106. Support beams 120 may also aide stiction mitigation during undercut and/or release of resonator 100 from a substrate. Support beams 120 can also be used to couple resonator to another structure. In some embodiments, support beams 120 can couple directly with a fixed portion of the substrate from which the resonator is etched.

In some embodiments, the dimensions of beams 110 and 111 are chosen so that their first flexural mode frequency is close to the first in-plane mode of resonator 100. This can be done, for example, in order to minimize acoustic loss through the support beams and/or to maximize resonator mechanical quality factors (Q). In some embodiments, the structures can be aligned to the 100 crystal orientation, where the absolute value of the longitudinal piezoresistive coefficient is at its maximum. This can be done, for example, to maximize the transduction coefficient of resonator 100.

Plates 105 and 106 can come in various sizes and/or shapes. For example, plates 105 and 106 can be a 10 μm×10 μm square. As another example, plates 105 and 106 can be 5 mm×5 mm square. Plates 105 and 106 can have one, two or three dimensions that are less than 500 μm, 400 μm, 300 μm, 200 μm, 100 μm, 50 μm, 20 μm, 10 μm, 5 μm, 1 μm, 800 nm, 600 nm, 400 nm, 200 nm, 100 nm, etc. Plates 105 and 106 can also be shaped as rectangles, circles, polygons, etc.

In some embodiments, resonator 100 can have a thickness that is less than 100 μm, 80 μm, 60 μm, 40 μm, 20 μm, 10 μm, 5 μm, 2 μm, 1 μm, 800 nm, 600 nm, 400 nm, 200 nm, 100 nm, 80 nm, 60, nm, 40 nm, 20 nm, 10 nm, etc. As another example, beams 110 and 111 can have widths less than 20 μm, 10 μm, 5 μm, 4 μm, 2 μm, 1 μm, 800 nm, 600 nm, 400 nm, 200 nm, 100 nm, 80 nm, 60, nm, 40 nm, 20 nm, 10 nm, etc. As yet another example, beams 110 and 111 can be 100 μm, 80 μm, 60 μm, 50 μm, 40 μm, 20 μm, 10 μm, 5 μm, 2 μm, 1 μm, 800 nm, 600 nm, 400 nm, 200 nm, 100 nm, 80 nm, 60, nm, 40 nm, 20 nm, 10 nm, etc., long.

Various processes can be used to fabricate resonator 100. FIG. 13 is an example of a flowchart of a process for fabricating a resonator according to some embodiments of the invention. At block 1305 and 1310 the plates and the beams are etched into a substrate. These can be etched in separate steps or in the same step. Pads (e.g., pads 425 shown in FIG. 4) and fixed masses (e.g., anchor 430 shown in FIG. 4) can also be etched into the substrate. Any number of etching or lithography techniques can be used to form the parts of the resonator. For example, wet chemical etching, dry etching, masking, deep reactive ion etching, photolithography, CMOS fabrication processes, etc., techniques can be used. At block 1315 the plates and beams can be suspended over the substrate using undercutting techniques. Once etched and possibly undercut, the plates and beams may undergo various post processing steps such as annealing and/or baking. These post processing steps may occur before or after undercutting. In some embodiments, the structures may be doped with dopants at block 1320. This doping may occur at any time during the process and may not occur at all.

In some embodiments of the invention, the motional conductance ($g_m$) for resonator 100 can be given by $$g_m = 4\alpha E^2 \pi_l Q \frac{A I_{dc}^2}{KLC_{th}\omega_m},$$

where $\alpha$, $E$, and $\pi_l$ are the thermal expansion coefficient, Young's modulus, and longitudinal piezoresistive coefficient of the structural material that resonator 100 is constructed from. A, L, and $C_{th}$ are the cross-sectional area, length, and thermal capacitance of beams 110 and 111. Q, K, $\omega_m$, and $I_{dc}$ are the quality factor, mechanical stiffness, resonance frequency, and bias current of resonator 100. As noted, motional conductance can depend on various physical properties of the resonator. As opposed to the passive piezoelectric or capacitive micromechanical resonators that typically have a positive (or dissipative) motional resistance; the motional conductance for a thermal-piezoresistive resonator can become negative provided that the structural material has a negative piezoresistive coefficient ($\pi_l$).

Figure 2A:
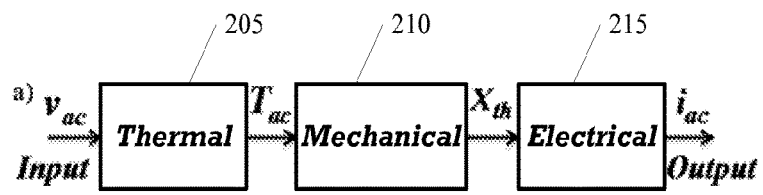
FIG. 2A shows a schematic diagram of the three physical domains involved in operation of thermal-piezoresistive resonators according to some embodiments of the invention.
Figure 2B:
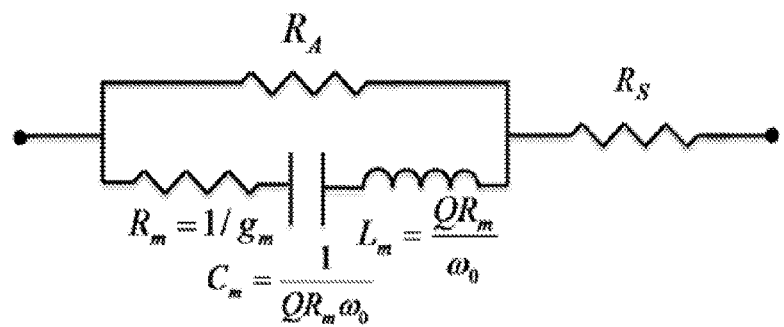
FIG. 2B shows an overall equivalent electrical circuit for a one-port thermally actuated resonator.

FIG. 2A shows a schematic diagram of the three physical domains involved in operation of thermal-piezoresistive resonators according to some embodiments of the invention. The input AC voltage causes a fluctuating thermal change at block 205, which causes a mechanical force in the actuators at block 210. This can result in mechanical vibrations at resonance frequency modulate the DC current in the actuators due to piezoresistive effect at block 215. FIG. 2B shows an overall equivalent electrical circuit for a one-port thermally actuated resonator with piezoresistive readout. $R_A$ is the electrical resistance of the actuators and $R_S$ is the parasitic resistance of the support beams.

A negative resistance (or negative conductance) is equivalent to an active energy pump. Therefore, thermal piezoresistive resonators can feed some energy back into their mechanical structure rather than just wasting energy through mechanical and/or ohmic losses as passive resonators do. If the absolute value of the negative motional conductance resulting from negative piezoresistive coefficient is increased to reach and surpass the value of $R_A^{-1}$, instead of the resonator losing part of its energy in every cycle, it can gain some extra energy in each cycle. This can lead to instability of the resonant system and self-sustained oscillation.

Figure 3:
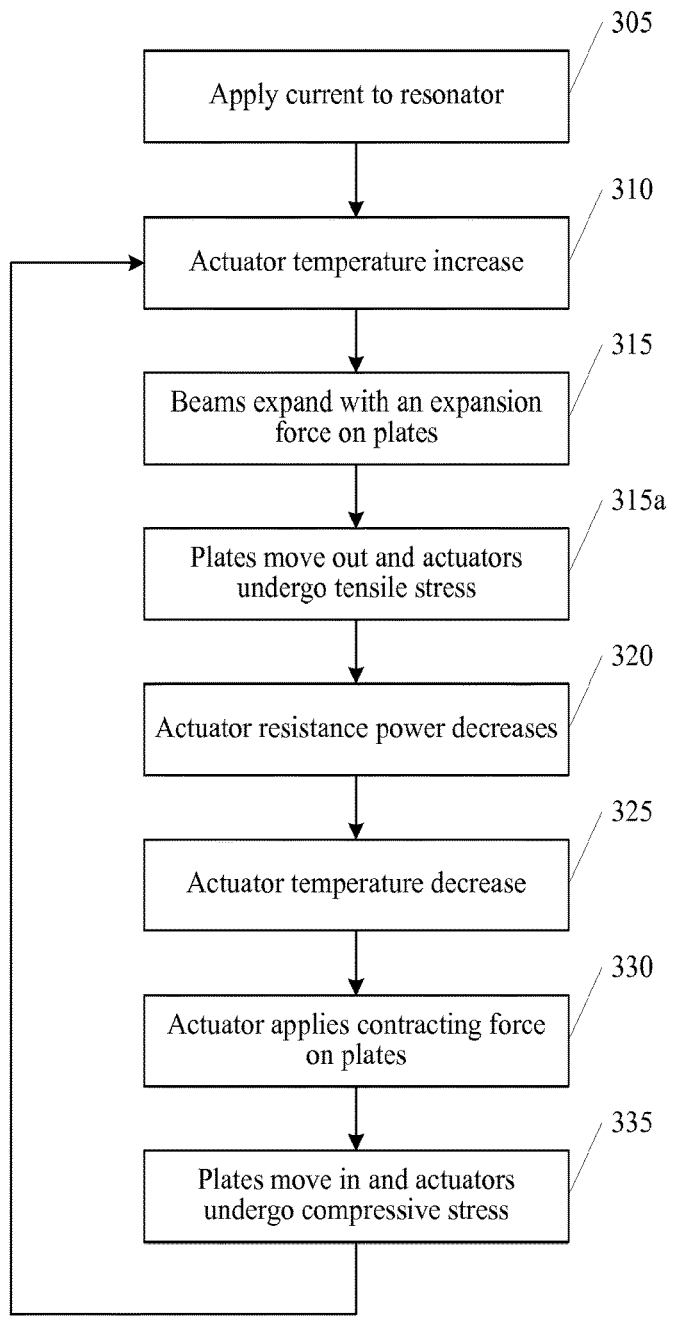
FIG. 3 shows a flowchart of the physical process that occurs within the resonator and according to some embodiments of the invention.

FIG. 3 shows a flowchart 300 of the physical process that occurs within the resonator that causes self-sustained oscillations according to some embodiments of the invention. A constant DC bias voltage can be applied at block 305. This bias voltage can produce a current in beams (e.g., beams 110 and 111) causing the beams to heat up at block 310. The heated beams can then expand at block 315. This expansion can push plates (e.g., plates 105 and 106) further away from each other. Because of the mass (inertia) of the plates, beams can experience an over-expansion after pushing the plates apart. This can result in tensile stress within the beams in block 315*a*. The negative piezoresistive coefficient causes the tensile stress to reduce electrical resistance in the beams at block 320, which can cause a reduction in the temperature of the beam at block 325. This reduction in ohmic power can force the beams to contract at block 330 with possible structural over-contraction. After structural over-contraction (due to the mass of the plates), the beams will be under compressive stress and will have increased electrical resistance at block 335. This again causes the beams to increase in temperature at block 310. If the resulting driving force (due to heating and cooling) in each cycle is large enough to compensate for mechanical losses of the structure, the same sequence is repeated over and over in a self-sustained manner and the vibration amplitude keeps increasing until it is limited by nonlinearities.

As noted above, simple periodic motion can occur by applying a DC bias across the beams. Because of the changes in resistance across the beams, with a constant current the voltage across the beams will vary in response to the changing resistance. Resonance can occur after a number of cycles producing a regular frequency response.

Figure 4:
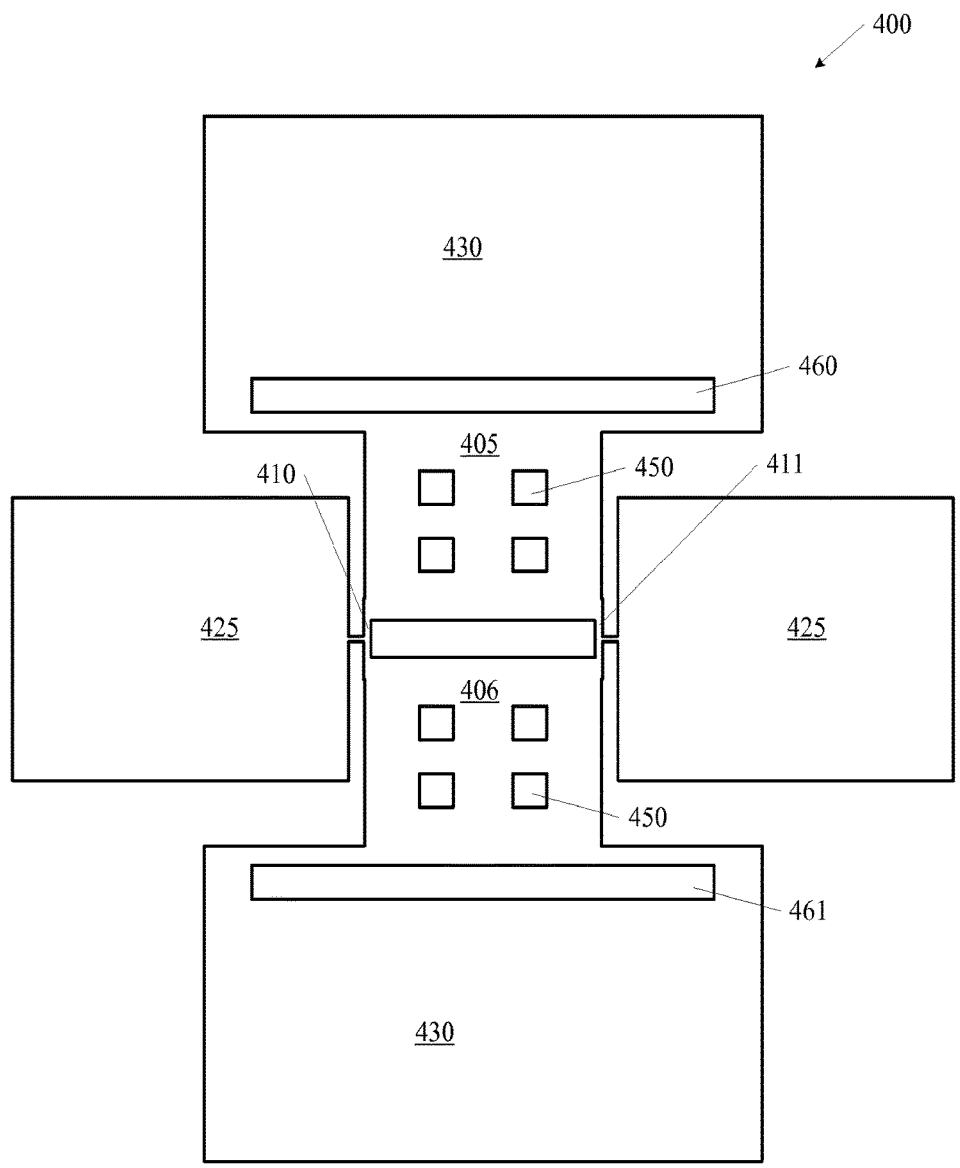
FIG. 4 shows another nano/micromechanical resonator according to some embodiments of the invention.

FIG. 4 shows another embodiment of a nano/micromechanical thermal resonator. Resonator 400 includes plate 405 and plate 406 connected together by beam 410 and beam 411. Beams 410 and 411 can be eclectically coupled with pads 425. DC bias current can be applied to beams 410 and 411 through pads 425.

Plates 405 and/or 406 can include a plurality of spacers 450 etched into the body of plates 405 and/or 406. These spacers can be used to control the mass of plates 405 and/or 406. These spacers can also be used to facilitate undercutting during fabrication. Plates 405 and 406 can also be coupled with fixed anchors 430. During oscillation plates 405 and 406 can oscillate relative to anchors 430. In some embodiments, anchors 430 can include gaps 460 and 461 that can aide in motion of plates 405 and 406. These gaps may also allow plates 405 and 406 to more easily vibrate relative to one another. Any number of gaps can be included. Moreover, plates 405 and/or 406 can have any size or shape.

Figures 5A, 5B, 5C:
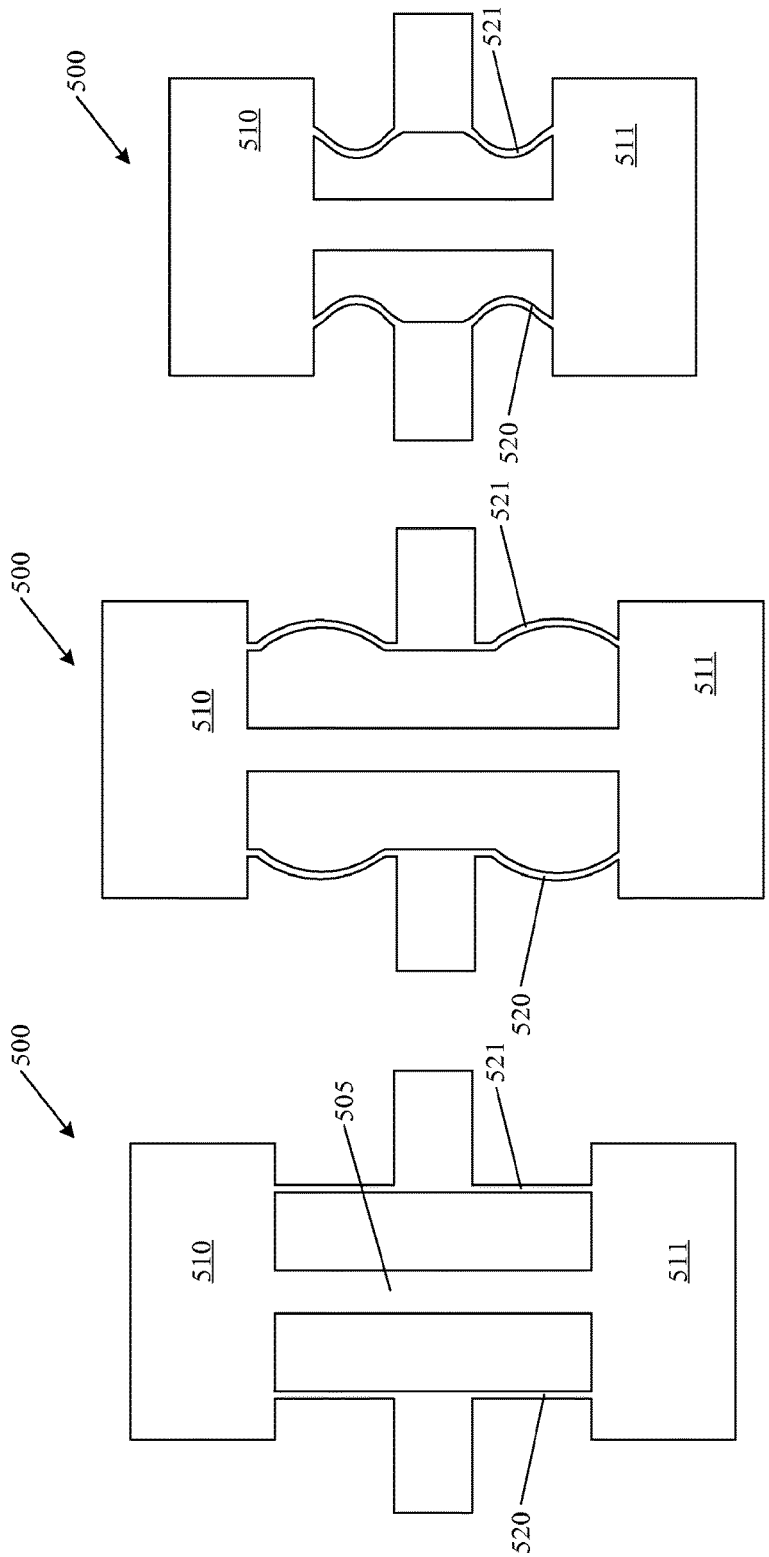
FIGS. 5A, 5B, and 5C show other embodiments of a micromechanical resonator in resting, stretched, and compressed states.

FIG. 5A shows another embodiment of a nano/micromechanical thermal resonator. Resonator 500 can include middle beam 505. Middle beam 505 can be wider than beams 510 and 511. In this embodiment, the resulting stiffness of the resonator is mainly determined by the wider middle bar. This can allow for higher resonance frequencies while maintaining very narrow beams 510 and 511. A wider middle beam may compensate for any manufacturing defects or changes in the dimensions of beams 510 and 511. Such defects will have less of an effect on the frequency of the resonator. Such embodiments can effectively decouple frequency variation from manufacturing defects resulting in lower manufacturing tolerances to produce resonators with similar frequency responses.

FIG. 5B shows resonator 500 in a stretched configuration. As shown beams 510 and 511 as well as middle beam 505 are stretched during one portion of the oscillation cycle. FIG. 5C shows resonator 500 in a compressed configuration. As shown beams 510 and 511 as well as middle beam 505 are compressed during another portion of the oscillation cycle. FIGS. 5B and 5C show resonator 500 90° out of phase.

Figure 6:
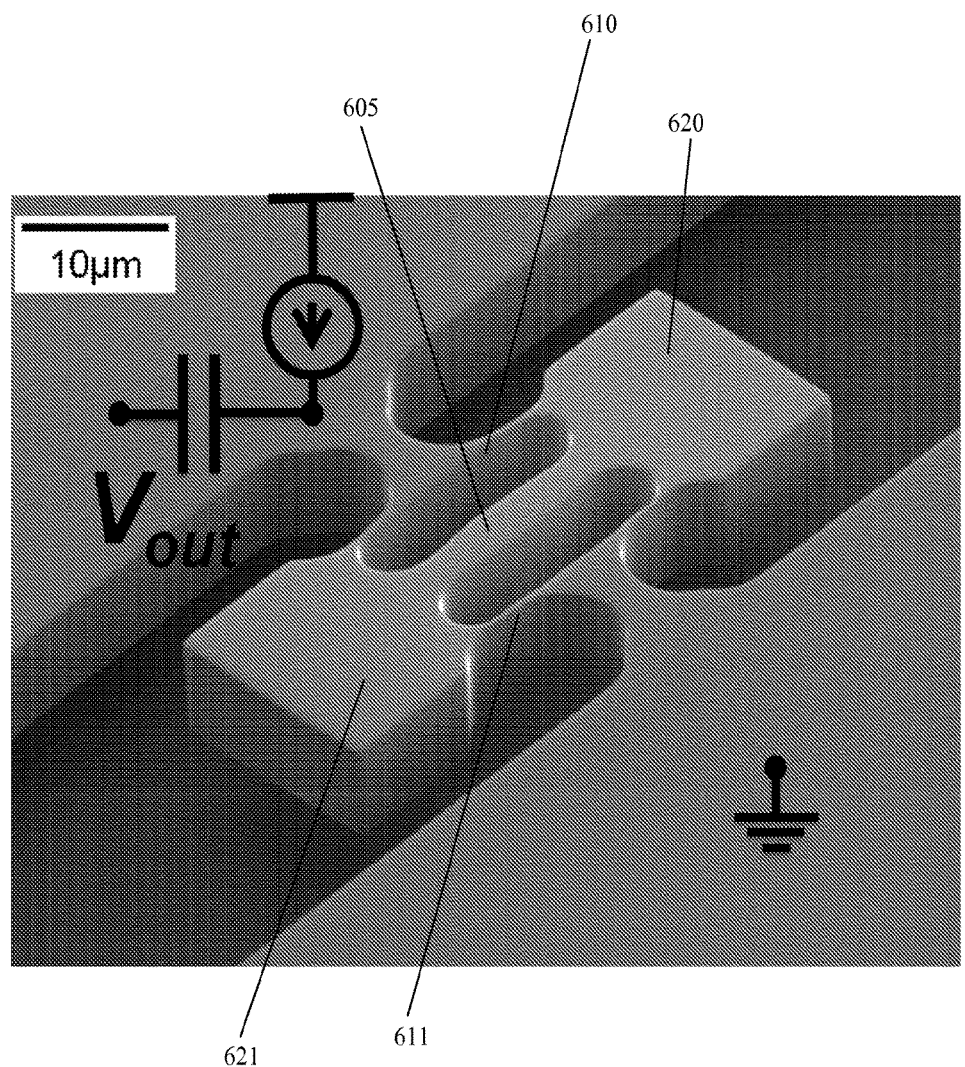
FIG. 6 shows a scanning electron microscope image of a resonator according to some embodiments of the invention.

FIG. 6 shows a scanning electron microscope image of resonator 600. Resonator 600 includes plates 620 and 621, beams 610 and 611, and middle beam 605. As indicated in the figure, a DC bias current is applied across beams 610 and 611. The voltage across these beams will then vary as the beams thermally expand and compress. In some embodiments, the output voltage may be tied to a decoupling capacitor as indicated.

Resonator 600 was fabricated using the standard single mask SOI-MEMS process on a low resistivity N-type SOI wafer with device layer thickness of 10 μm. Since longitudinal piezoresistive coefficient of silicon reaches its maximum value along the 100 direction, the resonator beams were fabricated along that direction for optimized transduction. Fabrication of resonator 600 included a series of thermal oxidation steps followed by oxide removal in hydrofluoric acid to narrow down the thermal actuators.

Instead of current sources relatively large resistors with values a few times (up to 10×) larger than the electrical resistance of the resonator, can be used to provide the resonator bias currents. By gradually increasing the bias current, after passing a threshold a fixed output frequency can be detected. In some embodiments, the output signal shape can be different than sinusoidal due to existence of different frequency harmonics. In this example, resonator 600 has its first in-plane resonance mode at 17.4 MHz, it can be concluded that the second harmonic is the dominant component. The first harmonic shows itself as uneven level of the consecutive peaks in the output waveform. In addition, the small ups and downs in the waveform can be blamed on higher frequency harmonics. By further increasing the bias current, the output voltage waveform constantly changes and at some point the first frequency harmonic with frequency of ~17.5 MHz becomes dominant.

Figure 7:
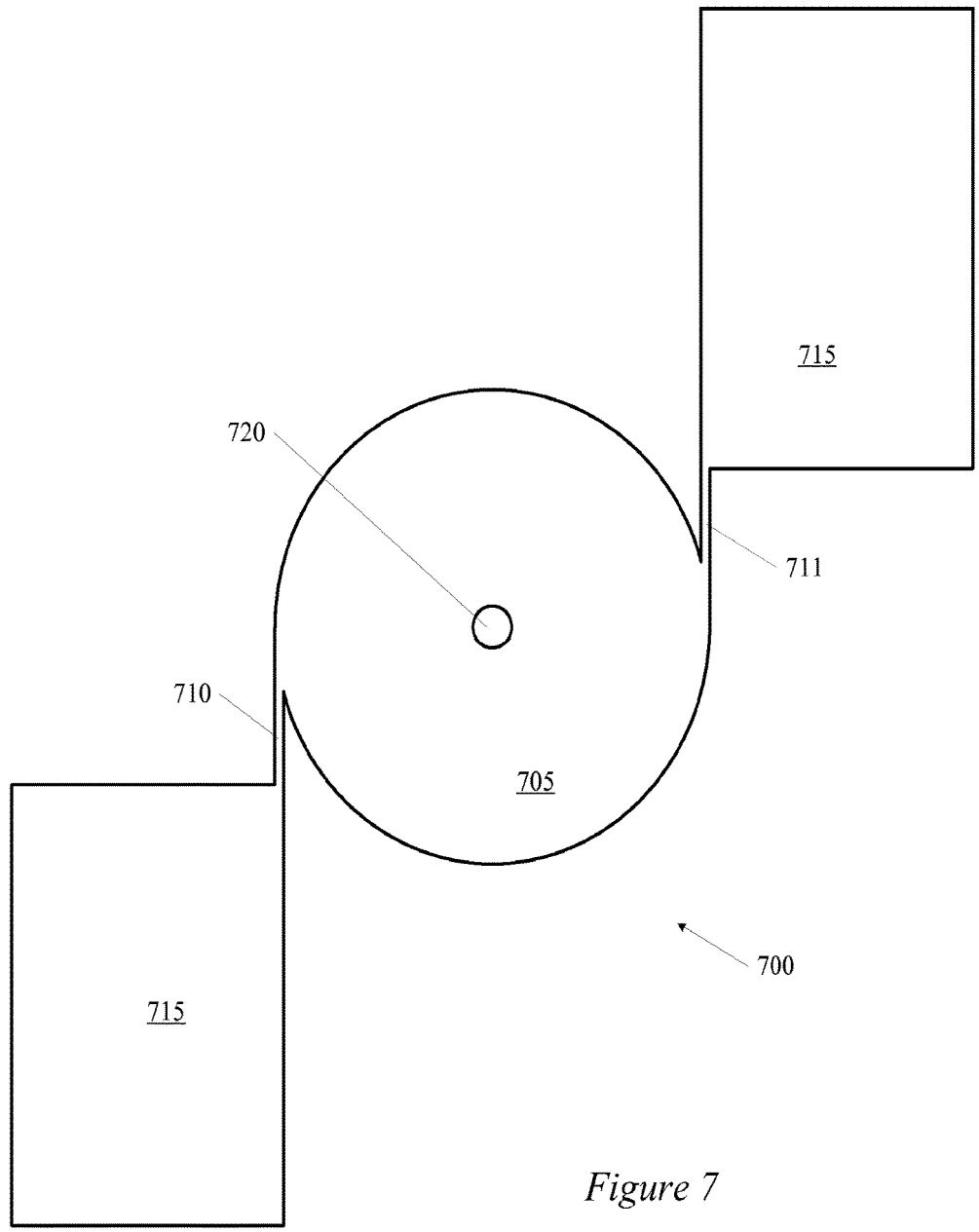
FIG. 7 shows the schematic view of resonator that includes a disk with straight tangential support beams according to some embodiments of the invention.

FIG. 7 shows a schematic view of resonator 700 that includes disk 705 with straight tangential support beams 710 and 711. Support beams 710 and 711 can act as thermal actuators and/or piezoresistive stress sensors. Thermal actuation can occur by passing a current through beams 710 and 711. This current can be applied to pads 715. In some embodiments, this current can include a combination of a DC current and an AC current, called the actuation current. Disk resonators can be useful for resonance applications in a liquid environment such as in biomedical applications.

In some embodiments, the ohmic power loss in resonator 700 can have a component at the same frequency as the applied AC current: $P_{ac}=2R_e I_{dc} i_{ac}$, where $R_e$ is the electrical resistance between the two pads and $I_{dc}$ and $i_{ac}$ are the applied DC and AC currents respectively. Due to their higher electrical resistance, most of the ohmic loss and therefore heat generation is concentrated in beams 710 and 711. The applied AC power can produce a periodic temperature fluctuation in beams 710 and 711 that can cause alternating stress and strain in the support beams (see e.g., FIG. 3). These stresses and strains can actuate disk 705 in its rotational resonance mode (periodically rotating back and forth around axis 720). As resonator 700 vibrates, the resulting periodic stress changes result in fluctuations in the electrical resistance of the resonator due to the piezoresistive effect. This modulates the DC current passing through the resonator leading to an AC output motional current component that can be used to monitor the resonator vibration amplitude.

While the disk is vibrating in its rotational mode, beams 710 and 711 can vibrate in their extensional mode (periodically elongating and contracting). As a result, all the surfaces of both the disk and its support beams move in parallel to the liquid interface, minimizing the energy loss to the surrounding liquid.

In some embodiments, disk 705 can have a diameter of 500 μm or less. The diameter of disk 705 can also be less than 400 μm, 300 μm, 200 μm, 100 μm, 50 μm, 20 μm, 10 μm, etc. Disk 705 and/or beams 710 and 711, for example, can have a thickness that is less than 100 μm, 80 μm, 60 μm, 40 μm, 20 μm, 10 μm, 5 μm, 2 μm, 1, μm, etc. For example, beams 710 and 711 can have width less than 20 μm, 10 μm, 5 μm, 4 μm, 2 μm, 1, μm, etc. As another example, beams 710 and 711 can have a length less than 100 μm, 80 μm, 60 μm, 40 μm, 20 μm, 10 μm, 5 μm, 2 μm, 1, μm, etc.

Figure 8:
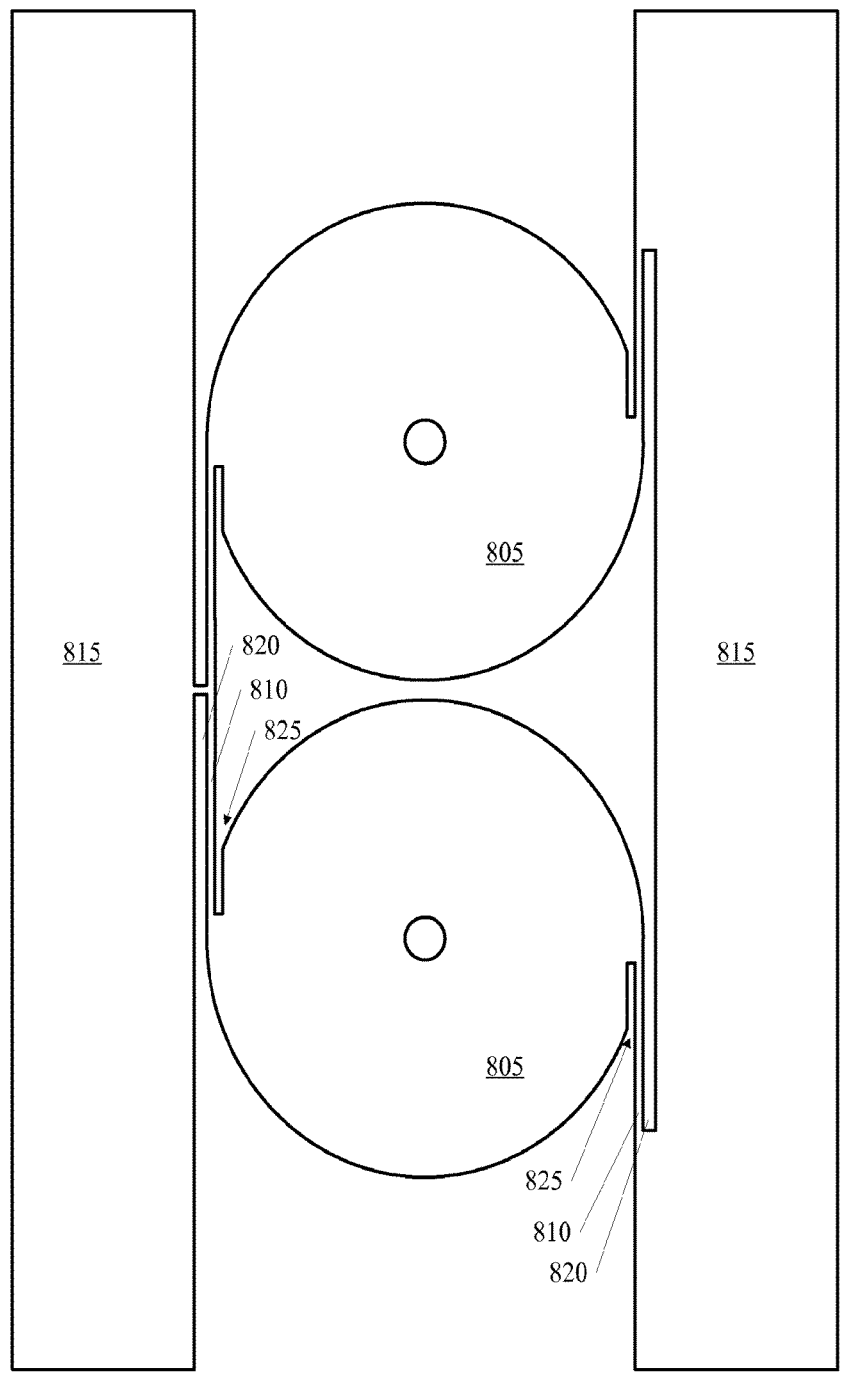
FIG. 8 shows two resonator disks in a parallel configuration according to some embodiments of the invention.
Figure 9:
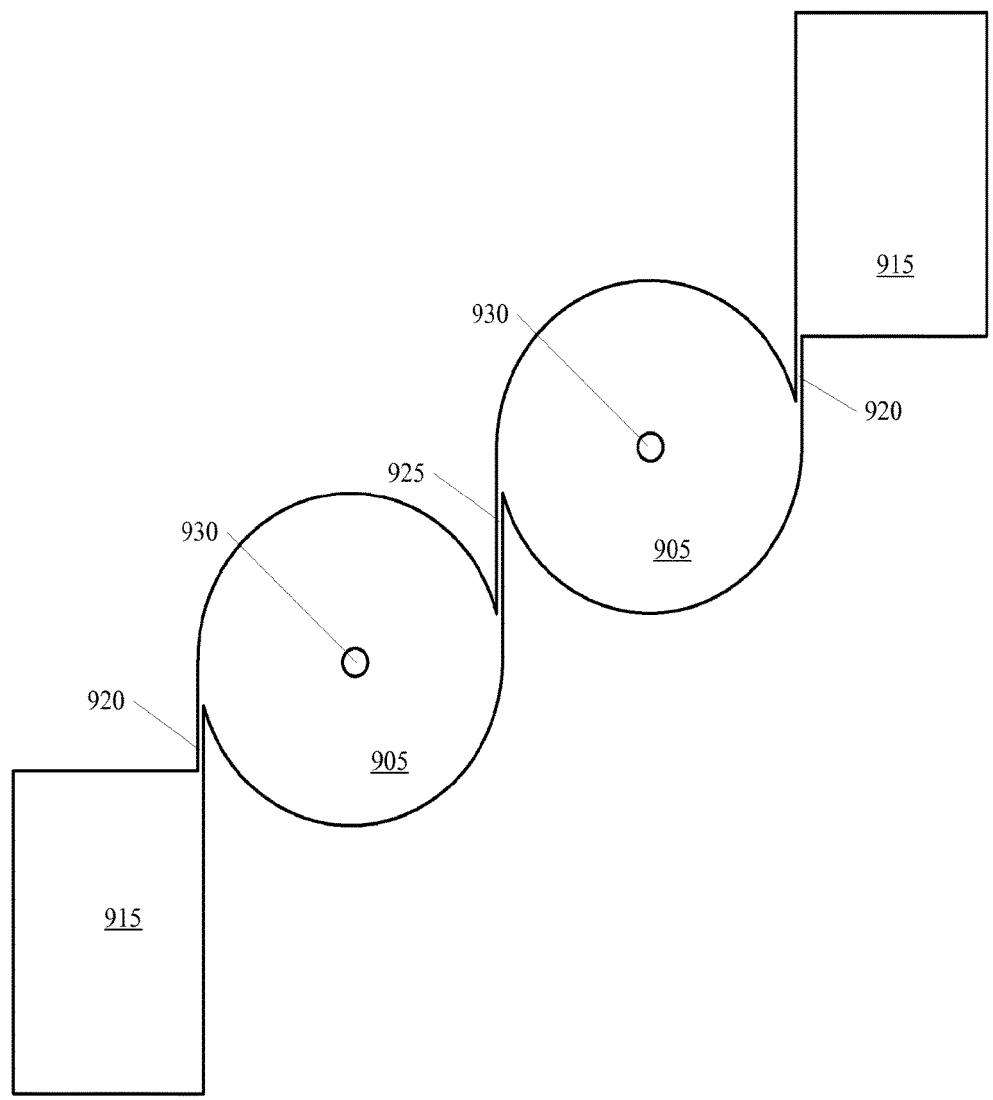
FIG. 9 shows two resonator disks in a series configuration according to some embodiments of the invention.

Various combinations of disk resonators can also be used. A few examples of such variations and combinations are shown in FIGS. 8 and 9. For example, FIG. 8 shows two resonator disks 805 in a parallel configuration. Resonators 805 include tangential support beams 810. Support beams 810 are coupled with anchors 815. Tangential support beams 810 can be coupled with resonator disks 805 with gaps 820 and anchors 815 with gap 825. More than two resonator disks 805 can be coupled together in parallel.

FIG. 9 shows two resonator disks in a series configuration. Resonator discs 905 are coupled together via beam 925 and with anchors 915 via beams 920. More than two resonator disks 905 can be coupled together in series. Moreover, multiple resonator disks can be coupled in series and parallel. Holes 930 can be formed in the middle of disk 905 are to aide in the undercut process.

Disk resonators (as well as any other resonators) can be fabricated, for example, using a standard single mask silicon-on-insulator microelectromechanical systems (SOI-MEMS) process. The fabrication process can include silicon deep reactive-ion etching (DRIE) to form the structures out of the silicon device layer, and releasing them by etching an underlying buried oxide (BOX) layer in hydrofluoric acid (HF). Resonators can be fabricated, for example, on a low resistivity N-type substrate with different device layers and/or BOX thicknesses. To optimize resonator electromechanical transduction, the support beams can be aligned to the crystalline direction where the longitudinal piezoresistive coefficients are maximum. Due to the circular shape of holes 930 and the relatively small vibration amplitude in the center of the disks such holes may have negligible effect on viscous damping of the resonator.

Figure 33:
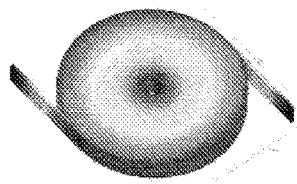
Figure 34:
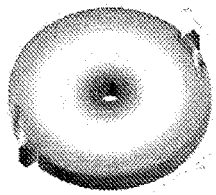
Figure 35:
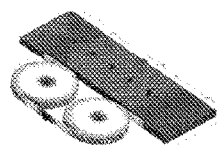
Figure 36:
Figure 37:

The following table summarizes measurement results for a variety of different disk resonators of different resonator types with different dimensions in both air and liquid. An example of a single disk resonator with a straight tangential support beam as discussed in the table is depicted in FIG. 33. A single disk resonator with a rounded support beam is shown in FIG. 34. FIG. 35 shows a parallel dual-disk resonator. FIG. 36 shows a series dual-disk resonator. An interconnected quad-disk resonator is depicted in FIG. 37. The table also shows the finite element modal analysis for different structures demonstrating the vibration amplitude at different parts of the structure. The modal analysis results show that unlike the other structures the interconnected quad-disks have an off-center rotation which justifies their lower Q in liquid despite their relatively high Q in Air.

In the following chart, "D" represents the diameter of the disk, "L" is the length of the beams and "H" is the thickness of the resonator. The table shows results for resonators in both air and heptane. The resonators tested typically have relatively low quality factors in air (due to excessive support loss). However, an unprecedented quality factor of 304 was measured in heptane. Such high Q values in heptane can be attributed to the elimination of the stroking surfaces from the mode shape.

| Type | Resonator Dimensions (μm) D | $L_{th}$ | H | Freq$_{Air}$ (MHz) | Q$_{Air}$ | Freq$_{Hep.}$ (MHz) | Q$_{Hep.}$ |
|---|---|---|---|---|---|---|---|
| Single Disk with Straight tangential support beam | 100 | 42 | 5 | 5.500 | 3500 | 5.500 | 145 |
| | | | 10 | 5.144 | 1900 | 5.144 | 175 |
| | | | 20 | 4.052 | 3000 | 4.052 | 215 |
| | | 17 | 5 | 6.827 | 2000 | 6.827 | 155 |
| | | | 10 | 6.427 | 1100 | 6.427 | 180 |
| | | | 20 | 5.356 | 1100 | 5.356 | 180 |
| | 200 | 55.5 | 5 | 2.586 | 4200 | 2.586 | 90 |
| | | | 10 | 2.383 | 700 | 2.383 | 170 |
| | | | 20 | 1.767 | 11700 | 1.767 | 110 |
| | | 35 | 5 | 3.368 | 2800 | 3.368 | 100 |
| | | | 10 | 2.849 | 3000 | 2.849 | 180 |
| | | | 20 | 3.056 | 1400 | 3.056 | 220 |
| Single Disk with Rounded support beam | 100 | 24 | 10 | 7.174 | 3500 | 7.174 | 235 |
| | | | 20 | 4.152 | 3800 | 4.152 | 230 |
| | | 11 | 5 | 7.366 | 1400 | 7.366 | 185 |
| | | | 10 | 8.406 | 600 | 8.406 | 195 |
| | | | 20 | 5.463 | 1700 | 5.463 | 304 |
| | 200 | 40 | 5 | 2.781 | 4900 | 2.781 | 95 |
| | | | 10 | 2.911 | 2600 | 2.911 | 230 |
| | | | 20 | 1.851 | 8500 | 1.851 | 160 |
| | | 24 | 5 | 3.394 | 4000 | 3.394 | 120 |
| | | | 10 | 3.513 | 1100 | 3.513 | 150 |
| | | | 20 | 2.616 | 5500 | 2.616 | 220 |
| Parallel Dual-Disk | 100 | 114 | 5 | 5.594 | 8000 | 5.594 | 125 |
| | | | 10 | 5.627 | 6500 | 5.627 | 105 |
| | | | 20 | 3.973 | 2000 | 3.973 | 180 |
| | | 103 | 10 | 5.350 | 7800 | 5.350 | 140 |
| | | | 20 | 3.752 | 2300 | 3.752 | 140 |
| Series Dual-Disk | 100 | 42 | 5 | 7.673 | 5000 | 7.673 | 170 |
| | | | 10 | 7.396 | 5000 | 7.396 | 180 |
| | | | 20 | 5.632 | 3200 | 5.632 | 180 |
| Interconnected Quad-Disk | 100 | 84 | 5 | 7.517 | 13500 | 7.517 | 155 |
| | | | 10 | 7.581 | 15000 | 7.581 | 150 |
| | | | 20 | 5.386 | 4800 | 5.386 | 50 |

Disk resonators can also be used in aqueous solutions. As such, disk resonators can be used, for example, in biotechnology applications.

Figure 14:
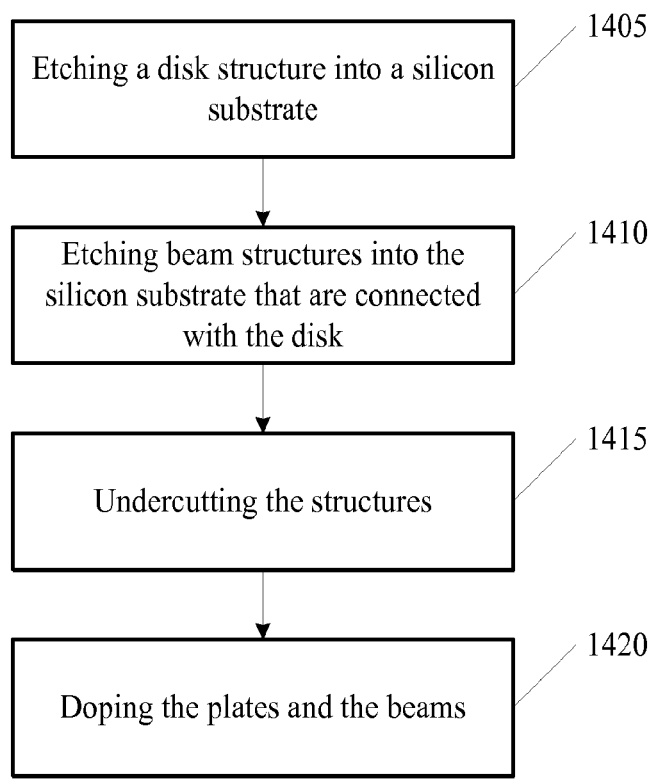
FIG. 14 is a flowchart of a process for fabricating a disk resonator according to some embodiments of the invention.

FIG. 14 shows a flowchart of a process for fabricating a disk resonator according to some embodiments of the invention. At block 1405 and 1410 the disk and the beams are etched into the substrate. These can be etched in separate steps or in the same step. Anchors 430 (e.g., anchors 715) can also be etched into the substrate. Any number of etching or lithography techniques can be used to form the parts of the resonator. For example, wet chemical etching, dry etching, masking, deep reactive ion etching, photolithography, CMOS fabrication processes, etc. techniques can be used. At block 1415 the disk and beams can be suspended on top of the substrate using undercutting techniques. Once etched and possibly undercut, the disk and beams may undergo various post processing steps such as annealing, doping, and/or baking. These post processing steps may occur before or after undercutting. In some embodiments, the disk and beams may be doped with dopants at block 1420. This doping may occur at any time during the process and may not occur at all.

Figure 10:
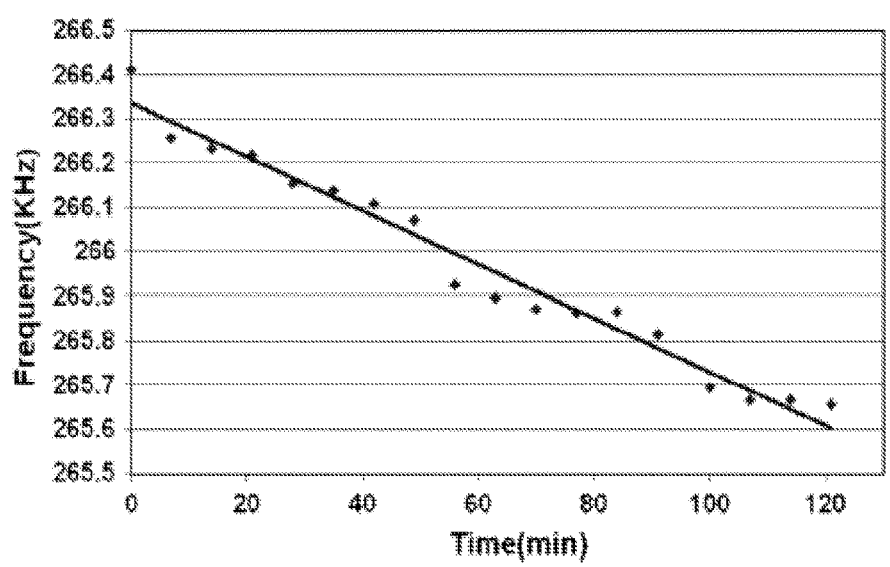
FIG. 10 is a graph showing the frequency response of a resonator to deposited particles using embodiments of the invention.

Embodiments of the invention can also be used as a particle mass sensor. The frequency response of any of the resonators described in the various embodiments of the invention can be inversely proportional to the square root of the mass of the resonator. As such, the frequency will change as the mass of the resonator changes. Because of this relationship, the frequency response will change as particles buildup on the mass of the resonators. FIG. 10 shows a graph of frequency measurements over time. As particles buildup on the masses of the resonators, the frequency of the resonator decreases in discrete steps.

Figure 11:
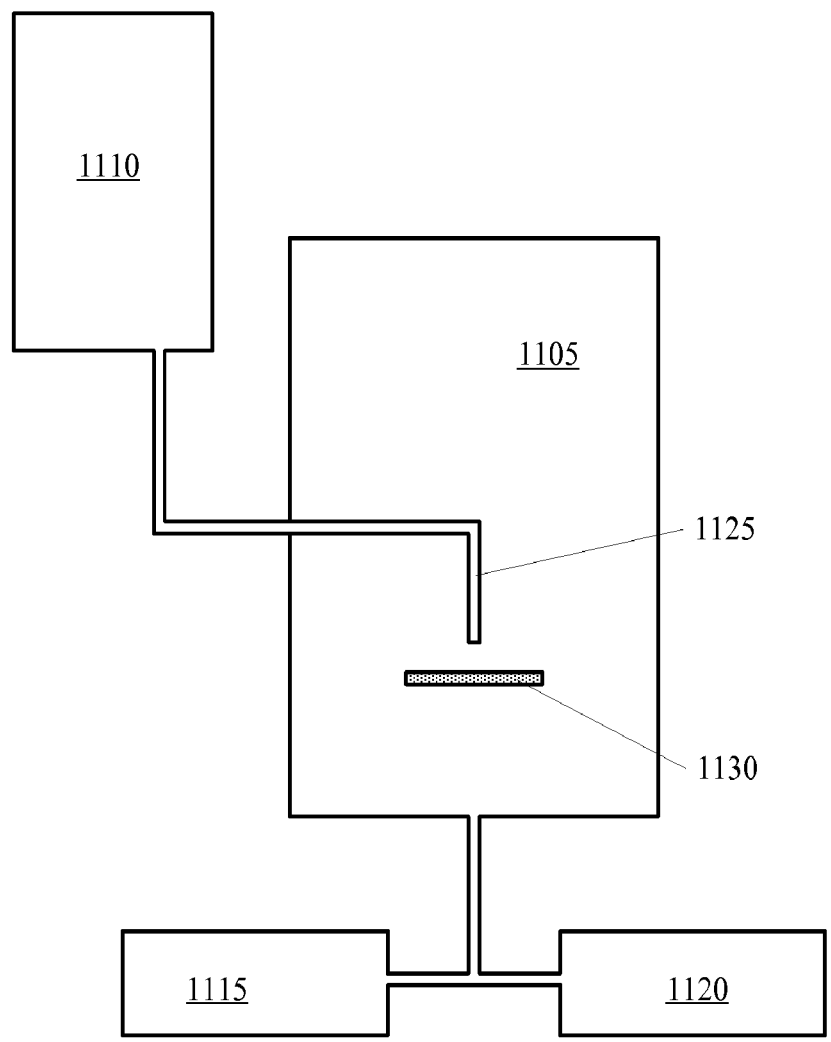
FIG. 11 is diagram of a particle mass sensor according to some embodiments of the invention.

FIG. 11 shows an embodiment of a particle mass sensor according to some embodiments of the invention. Chamber 1105 can house mass sensor substrate 1130 comprising one or more resonators positioned below particle nozzle 1125. Nozzle 1125 can be placed, for example, around 1 mm from substrate 1130. Pump 1120 can be used to maintain a low pressure within chamber 1105 and pressure sensor 1115 can measure the pressure within chamber 1105. Particles from particle source 1110 can be sucked onto sensor 1130 due to low pressure in the chamber. When actuation voltages or currents are applied to mass sensor 1130, the frequency of the micromechanical resonator can be measured. The mass of particles deposited on sensor 1130 can be determined in real time by measuring the resulting change in frequency.

Figure 12:
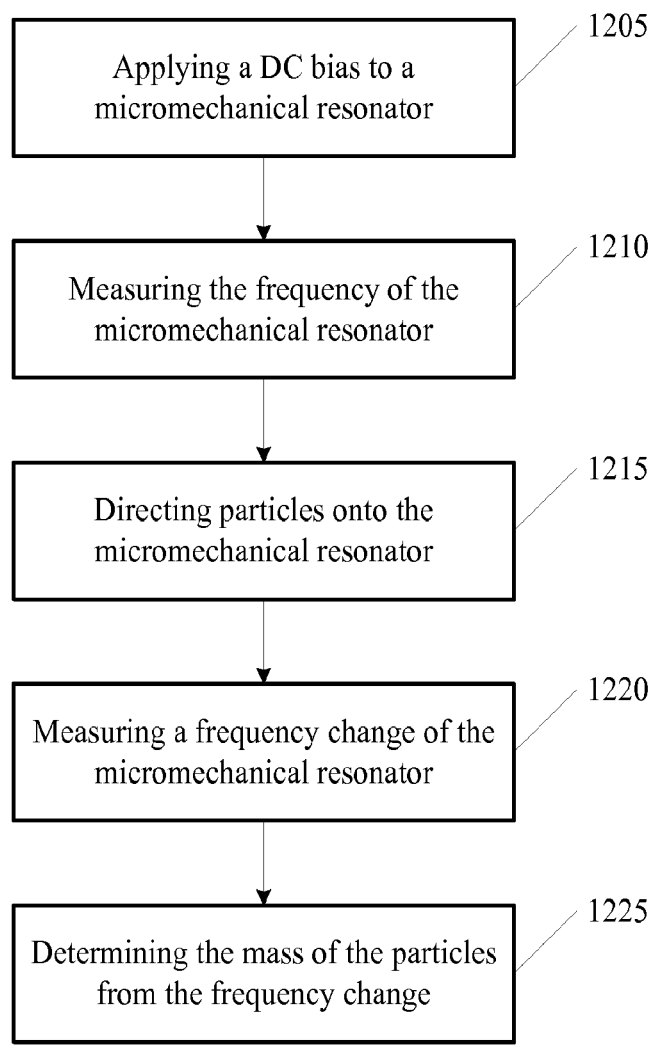
FIG. 12 is a flowchart of a process for sensing the mass of particles according to some embodiments of the invention.
Figure 13:
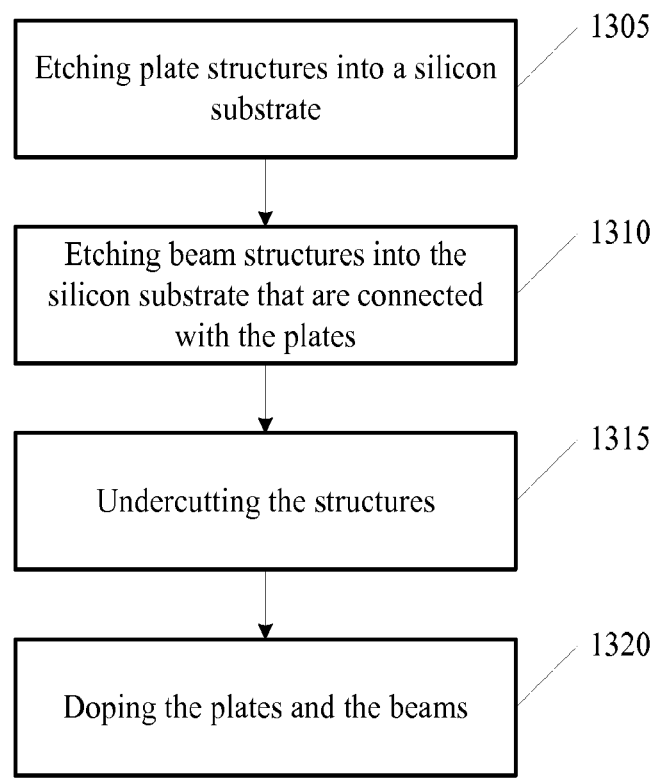
FIG. 13 is a flowchart of a process for fabricating a resonator according to some embodiments of the invention.

FIG. 12 is a flowchart of a process for sensing the mass of particles according to some embodiments of the invention. At block 1205 a DC bias current is applied to micromechanical resonator. The resonator can be any of the resonators described herein or any other micromechanical resonator known in the art. In some situations, the resonator may need some time to stabilize and/or come to resonance. At block 1210 the frequency of the resonator can be measured. This frequency can be noted as the baseline frequency.

At block 1215 particles can be directed on to the resonator. These particles can be directed onto the resonator, for example, through nozzle 1025. In some embodiments, the particles can be in a pressurized vessel and directed toward the resonator under pressure. As the particles land on, adhere, rest, stick, etc. to the resonator, the mass of the plates change causing a change in the frequency response. This frequency can be measured at block 1220. The mass of the particles can be determined at block 1225.

Silicon can become softer as temperatures rise and stiffer as temperatures lower. Changes in stiffness resulting from temperature can change the frequency of the resonator. This temperature drift of frequency can be as much as −40 ppm/° C. Because the actuator beams used in the resonators described herein are made from silicon, the softening and/or stiffening of silicon can affect the frequency of the resonator. To reduce the frequency's temperature dependency, the silicon can be doped with various dopants. For example, the silicon can be doped with boron, creating p-type silicon, or doped with phosphorus, creating n-type silicon. These dopants can be added before or after resonator fabrication. Other types of dopants may also be used. These may include, for example, germanium, arsenic, antimony, aluminum, gallium, etc. In some embodiments, group 3 or group 5 elements.

In some embodiments, the DC bias current can be adjusted to compensate for the temperature drift. For example, raising the bias current can lead to a more positive temperature drift coefficient and lowering the bias current can lead to a more negative temperature drift coefficient. In some embodiments, the resonators can be both doped and use current compensation to correct for temperature drift. Thus, a resonator fabricated from doped materials can have a substantially lower temperature drift. In some cases, a doped resonator can have a drift that is near zero (e.g., between 2 ppm/° C. and −2 ppm/° C.). A small adjustment to the DC bias can move the drift nearer to or to zero (e.g., changing the current from 1.3 mA to 1.33 mA). Thus a combination of doped materials and DC bias adjustments can compensate for temperature drift.

Figure 15:
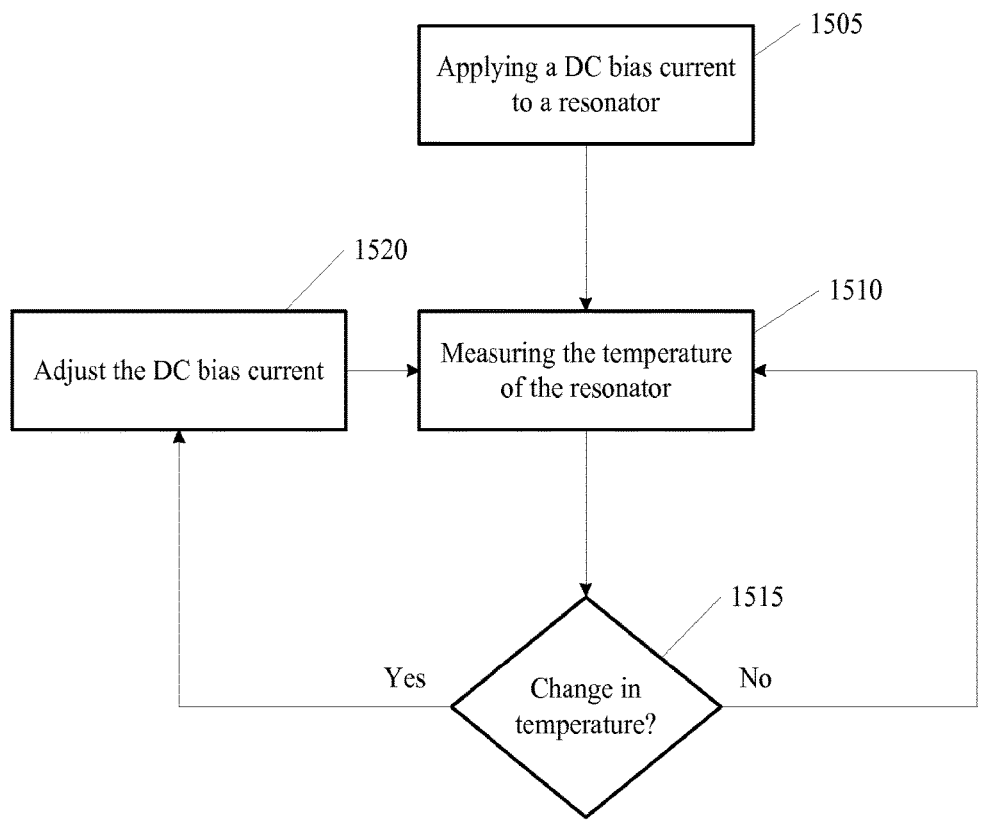
FIG. 15 is a flowchart of a process for compensating for temperature drift according to some embodiments of the invention.

Temperature compensation can also occur in an active manner. FIG. 15 shows a flowchart of a process to perform active frequency compensation according to some embodiments of the invention. At block 1505 a DC bias current is applied to a resonator. In some situations, like disk resonators, an AC bias current may also be applied. The temperature of the resonator can be measured at block 1510. At block 1515, the process can determine if a frequency drift is occurring by monitoring the temperature over time. Because temperature and frequency are related, a noted change of temperature signifies a change in frequency. If there is temperature change then the process simply repeats by returning to block 1510. If the temperature is changing, as determined at block 1515, then the DC bias current can be adjusted at block 1520. If the temperature change is positive then the bias current can be increased. If the temperature change is negative then the bias current can be decreased.

The following table summarizes measured TCF values for a number of different test resonators. The trend observed in all the doped resonators is that when operated at higher bias currents (higher static temperature) the TCF values become more positive (or less negative). This could be explained by the elevated temperature having a similar effect on the band structure of silicon as degenerate doping. By having the right doping level and bias current, potentially zero TCF can be achieved for such devices.

In the following table "a" represents is the width of the plates and "b" is the length of the plates. "H" represents the thickness of the resonator, "L" the length of the beams, and "W" the width of the beams.

interface 1650 can be a USB interface, UART interface, serial interface, parallel interface, etc. Resonator interface 1650 can be configured to couple directly with any type of resonator system or particle mass sensing system.

The controller 1600 also comprises software elements, shown as being currently located within working memory 1620, including an operating system 1624 and other code 1622, such as a program designed to implement methods and/or processes described herein. In some embodiments, other code 1622 can include software that provides instructions for the various processes described herein. In some embodiments, other code 1622 can include software that can perform the various functions or processes described herein. It will be apparent to those skilled in the art that substantial variations can be used in accordance with specific requirements. For example, customized hardware might also be used and/or particular elements might be implemented in hardware, software (including portable software, such as applets), or both. Further, connection to other computing devices such as network input/output devices can be employed.

Controller 1600 can be used, for example, to perform any or all the computations shown in or described in conjunction with FIGS. 12-15. Controller 1600, for example, can be used to compute particle mass values from frequency measurements and/or temperature drift changes from frequency values. In some embodiments, when coupled to a MEMS

| Resonator Dimensions (µm) | | | | | Actuator Tilt | Freq. | | Bias Current | $R_{DC}$ | $g_m$ | Power | Phos. Dope @ 950° C. | Annealed @ 1100° C. | TCF |
|---|---|---|---|---|---|---|---|---|---|---|---|---|---|---|
| A | b | L | W | H | Angle ° | (MHz) | $Q_{air}$ | (mA) | (Ω) | (µS) | (mW) | | (hours) | PPM/° C. |
| 200 | 200 | 20 | 4 | 5 | 45 | 3.78 | 4800 | 45.3 | 11.5 | −29.5 | 23.5 | 2 hours | 7 | 1.13 |
| | | | | | | | 3900 | 59.5 | 11.5 | −52.6 | 40.7 | | | 1.18 |
| 100 | 100 | 6 | 2 | 5 | 0 | 6.59 | 9000 | 34.4 | 10 | −78.4 | 11.8 | | | 0.32 |
| | | | | | | | 11000 | 52.1 | 10 | −167 | 27.1 | | | 0.79 |
| 30.2 | 20.2 | 30.8 | 0.2 | 2.2 | 15 | 8.21 | 7500 | 1.07 | 155 | — | 0.18 | | 2.5 | −0.54 |
| | | | | | | | 7000 | 1.30 | 155 | — | 0.26 | | | −0.05 |
| 30.6 | 20.6 | 14.9 | 0.6 | 2.6 | 0 | 23.2 | 2550 | 5.31 | 50.5 | −175 | 1.42 | | | 0.67 |
| 15 | 10 | 11.7 | 0.8 | 3.5 | 0 | 60.6 | 490 | 12.5 | 46.5 | −260 | 7.29 | | | −2.4 |
| | | | | | | 59.2 | 395 | 17.1 | 46.5 | −510 | 13.6 | | | −1.8 |

Figure 16:
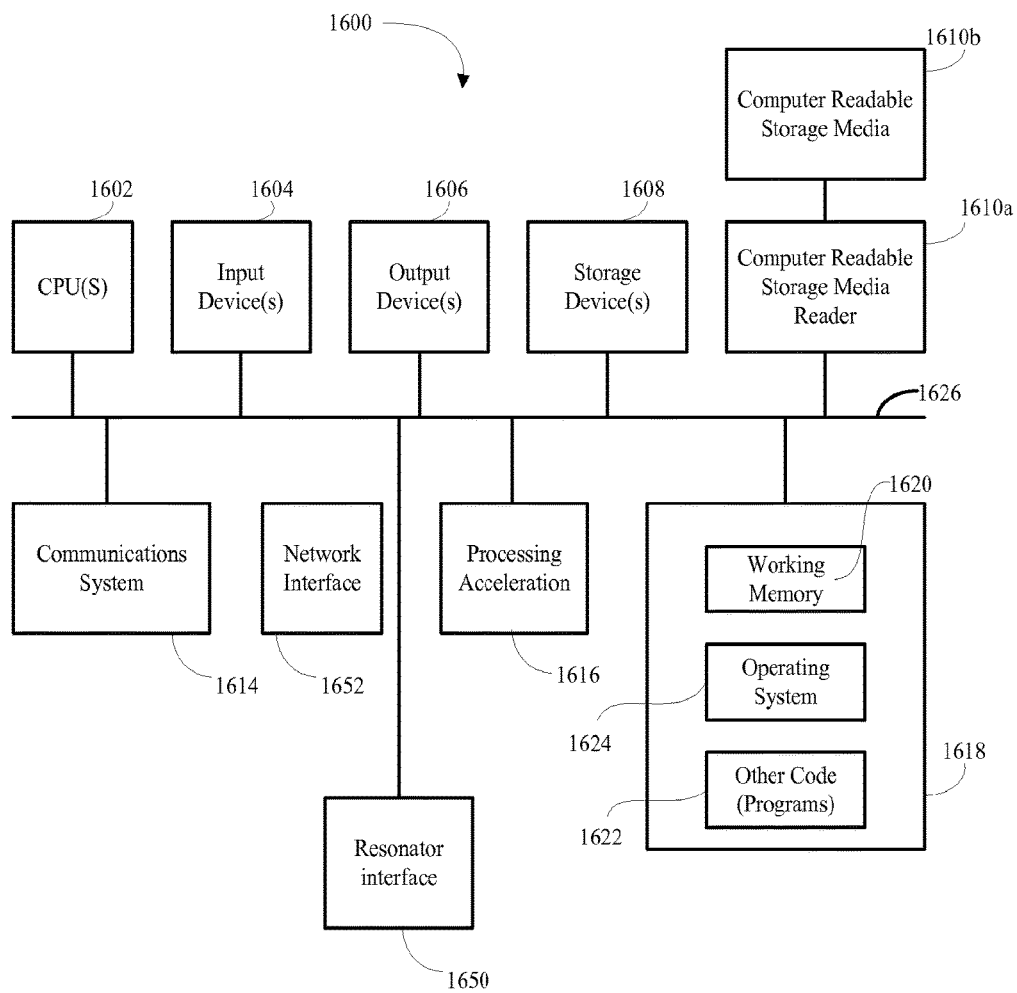
FIG. 16 shows a simplified block diagram of a computational system that can be used to implement embodiments of the invention.

FIG. 16 shows a simplified block diagram of a controller 1600 that can be coupled with a resonator and/or a sensor for computation purposes according to embodiments of the invention. The drawing illustrates how individual system elements can be implemented in a separated or more integrated manner. The controller 1600 is shown having hardware elements that are electrically coupled via bus 1626. Network interface 1652 can communicatively couple the controller 1600 with a computer, for example, through a network such as the Internet. The hardware elements can include a processor 1602, an input device 1604, an output device 1606, a storage device 1608, a computer-readable storage media reader 1610a, a communications system 1614, a processing acceleration unit 1616 such as a DSP or special-purpose processor, and memory 1618. The computer-readable storage media reader 1610a can be further connected to a computer-readable storage medium 1610b, the combination comprehensively representing remote, local, fixed, and/or removable storage devices plus storage media for temporarily and/or more permanently containing computer-readable information.

Resonator interface 1650 is coupled with bus 1626. In some embodiments, resonator interface 1650 can be any type of communication interface. For example, resonator resonator via an electrical bus, controller 1600 can read frequency data from the MEMS resonator, calculate shifts in the resonant frequency, and determine the particulate concentrations in real-time. The controller 1600 can be configured to indicate the concentration levels to users in real-time as well. For example, controller 1600 could display the concentration levels or trends in the concentration levels on a display, or the controller 1600 could produce an audio and/or visual signal to alert a user that a user-programmed threshold had been reached.

Figure 17:
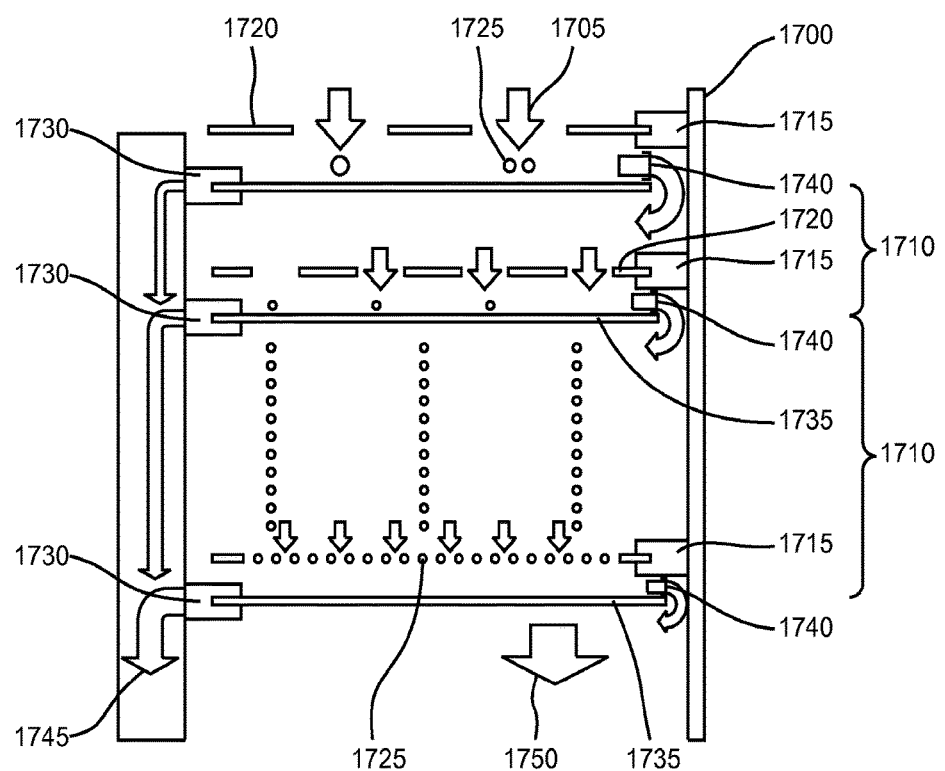
FIG. 17 shows the schematic view of a micromachined cascade impactor with integrated MEMS resonant balance arrays according to some embodiments of the invention.

FIG. 17 depicts an embodiment of cascade impactor 1700 which is connected to an aerosol source. In some embodiments the entire impactor can be the size of a pen, or smaller, and can be battery powered. Cascade impactor 1700 comprises an air intake opening 1705. Air can flow from air intake opening 1705 into a series of impactor stages 1710. Each sequential impactor stage 1710 can operate with the output of one stage feeding the input of the next. The final impactor stage 1710 can be connected to an air flow device 1750 that maintains a low pressure environment within cascade impactor 1700 in order to draw in air from air intake opening 1705 to be tested for particulate content. In some embodiments air flow device 1750 is a vacuum pump.

Each impactor stage 1710 can have a corresponding nozzle plate 1720 fixed to a support housing 1715. Each nozzle plate 1720 includes one or more openings 1725 of specified diameters. These diameters decrease from upper to lower impaction stages 1710. Openings 1725 can be micromachined in silicon chips by etching through holes via DRIE. Impaction plates 1735 can be aligned below corresponding nozzle plates 1720 and fixed to a support housing 1730, while not obstructing the incoming airflow to other impactor stages. Impaction plates 1735 with diameters in the few millimeter range can be fabricated out of silicon wafers via standard micromachining techniques. As air passes through openings 1725 in nozzle plates 1720, it can be accelerated, forming jets to effectively direct particles onto the impaction plates 1735. Particles with diameters smaller than a cut-point diameter 1740 within each impactor stage 1710 will escape collision with the impaction plate 1735 and move on to the next impactor stage 1710. Particles larger than the cut-point diameter 1740 are deposited on the impaction plate 1735. The cut-point diameters 1740 and pressure levels decrease from stage to stage. In some examples, cut-points are as small as 10 nm.

Figure 19:
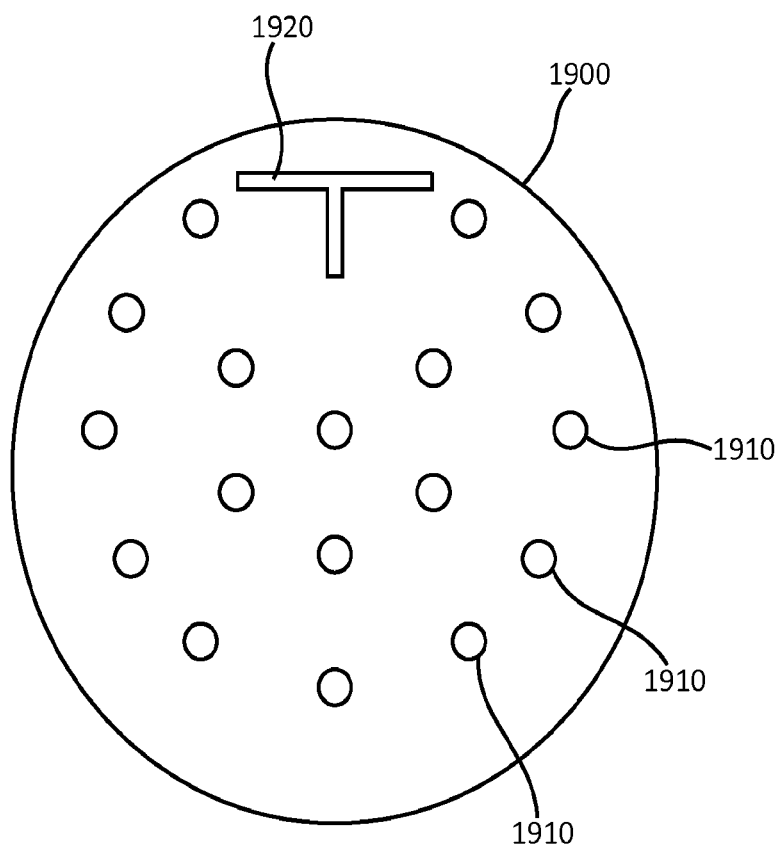
Figure 20:
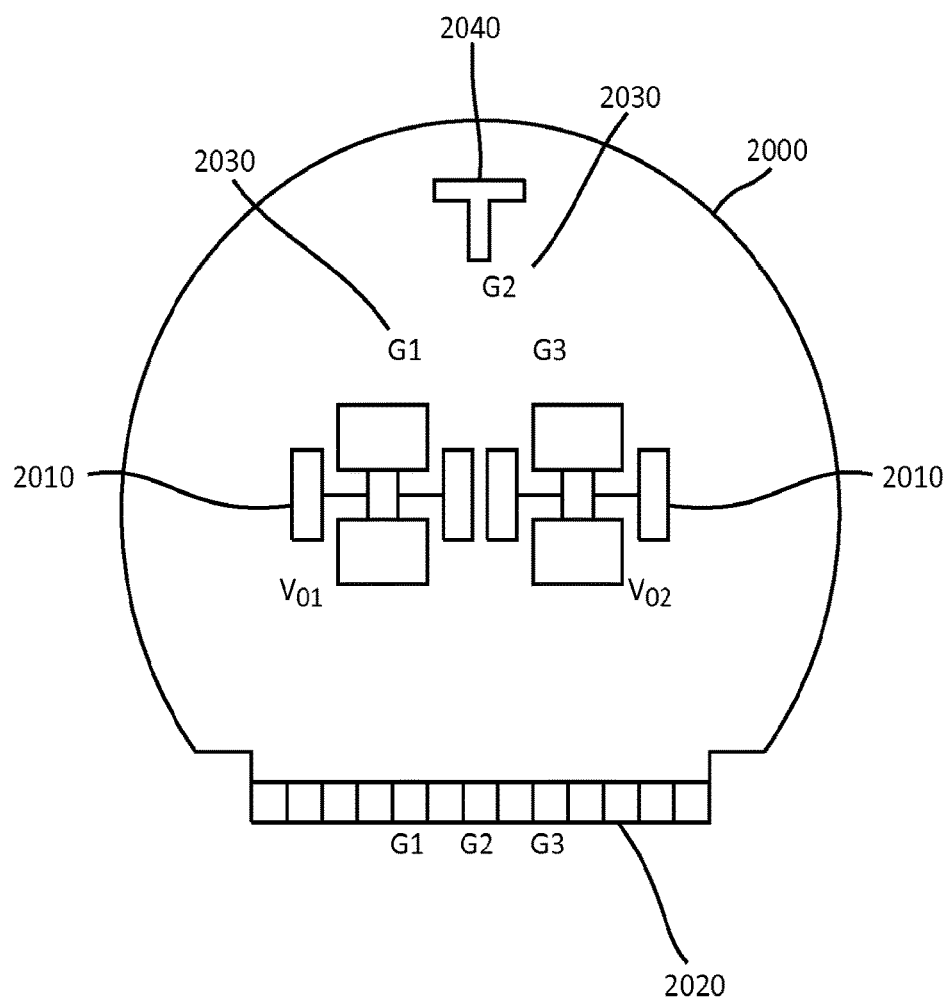
Figure 21:
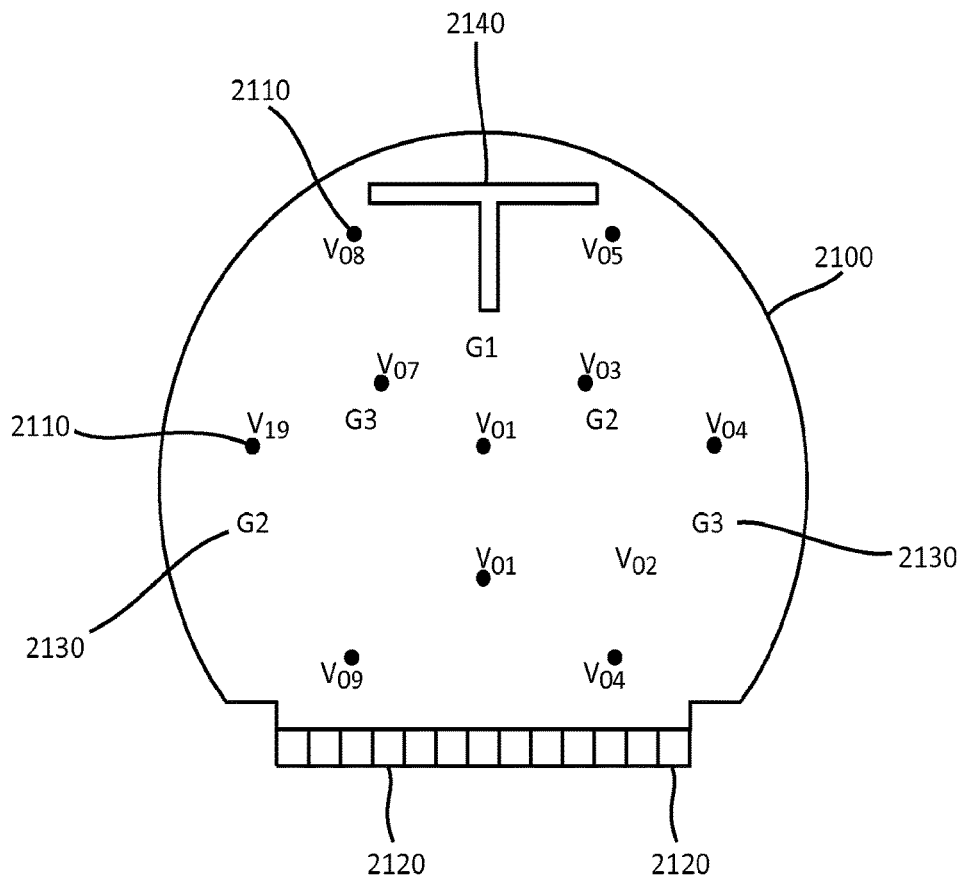

Some embodiments include an alignment structure 2200 (FIG. 22) that can couple with slots in nozzle plates (FIGS. 18 and 19) and slots in impaction plates (FIGS. 20 and 21). Alignment structure 2200 can be stepped to provide for proper vertical spacing between each impaction stage's 1710 corresponding nozzle plate 1720 and impaction plate 1735. Additionally, alignment structure and slots in some embodiments can have T-shaped cross-sections in order to fix the alignment in multiple dimensions. In some embodiments alignment structure 2200 is carved out of silicon substrates by DRIE.

Figure 1:
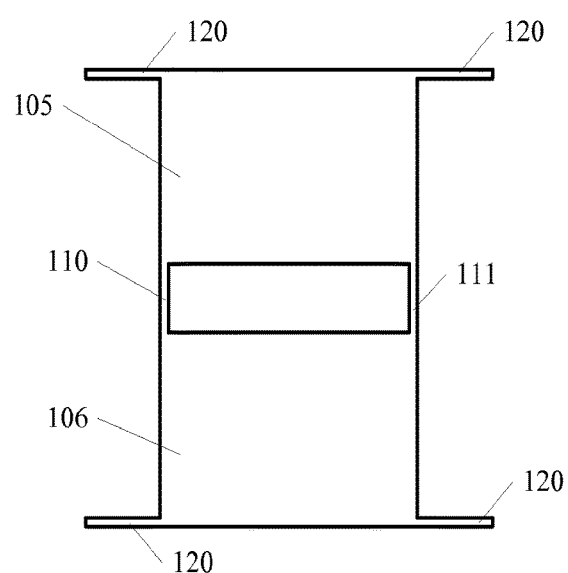
FIG. 1 shows an in-plane resonator according to some embodiments of the invention.

Impaction plates 1735 can contain MEMS resonators 100 or arrays of MEMS resonators 100. The resonator can be any of the resonators described above, such as those described in FIG. 1, or any other micromechanical resonator known in the art. MEMS resonators 100 can be manufactured as small as 0.01-2 mm$^2$ and can provide high mass sensitivity on the order of a few femto-grams, if not lower. The small size of the resonators allows their integration into arrays providing redundancy as well as a larger sensitive area. More particles can be detected by an array with fewer particles being deposited on any single resonator, prolonging the lifetime of the resonator. Some embodiments have up to tens of resonators included in each stage. Particle mass is calculated by adding all the responses of the resonators and accounting for the sensitive area of the resonators. Due to the self-oscillation capability of MEMS resonators, the analog electronic circuitry for driving each electromechanical resonator into oscillation is eliminated. The remaining circuitry required to frequently measure and record the frequency of each device would be digital with the exception of a simple amplification stage at the output of each resonator which may or may not be required.

MEMS resonators 100 have a uniform mass sensitivity over the resonator area, meaning that regardless of where on the resonating plates a particle is placed, the resulting frequency shift in the resonator will be the same. The uniform resonator area, coupled with high mass sensitivity, enables MEMS resonators 100 to measure mass of every single micro/nanoscale particle landing on their surface. This reduces the number of impactor stages required for particle size segregation because each resonant balance can provide a precise mass measurement for each particle within a wider size range. TPRs, such as MEMS resonators 100, can handle deposition of a significant amount of particulate mass and continue to operate seamlessly with hundreds to thousands of micro/nanoscale particles deposited on their vibrating plates. The high sensitivity and capability to collect data on every single particle leads to statistically valid data on particle size distributions. Tens of thousands to millions of particles can be sampled by an array consisting of tens of resonators in each measurement cycle.

Impaction plates 1735 can measure the mass of incoming aerosol particles by monitoring shifts in the resonance frequency of the resonators. Shifts in resonance frequency occur when they are loaded with particles. The resonant frequency is given by:

$$f = \frac{1}{2\pi}(1/2p)\sqrt{\frac{k}{m}} \Rightarrow \frac{\partial f}{\partial m} = -\frac{f}{2m},$$

where k, m, and f are the effective stiffness, effective mass, and resonant frequency of the resonator, respectively.

Impaction plates 1735 can be of varying sensitivity levels, with the lowest sensitivity levels being in the upper stages where the largest particles are detected. Impaction plates 1735 can be designed such that one or more MEMS resonators 100 are placed underneath some of the openings 1725 with microscale precision. High precision horizontal alignment can be achieved between the plates using vertically placed micromachined pieces of silicon passing through micromachined slots etched into the nozzle plate 1720 and impaction plate 1735.

Impaction plates 1735 are electrically coupled to at least one electrical bus 1745 whereby impaction plates 1735 are supplied with power from a power source. For example, one power source may be a battery. Measurement and processing circuitry can also be attached via electrical bus 1745. Additionally, in some embodiments, electrical bus 1745 couples to a field programmable gate array (FPGA) to integrate digital components, including the measurement and processing circuitry into one chip. Further embodiments include a PC or other real-time display module connected through electrical bus 1745.

Cascade impactor 1700 containing MEMS resonators 100 can be fabricated in various sizes and shapes. For example cascade impactor 1700 can be a 10 cm×1 cm×1 cm cylinder. Cascade impactors 1700 can have one, two, or three dimensions that are less than 100 cm, 75 cm, 50 cm, 25 cm, 10 cm, 5 cm, 3 cm, 2 cm, and 1 cm, etc. In some embodiments, cascade impactor 1700 can have a volume of less than 400 cm$^3$, 200 cm$^3$, 100 cm$^3$, 50 cm$^3$, 40 cm$^3$, 25 cm$^3$, 10 cm$^3$, 5 cm$^3$, 3 cm$^3$, 2 cm$^3$, 1 cm$^3$, etc. Cascade impactor 1700 can also be shaped as rectangular prisms, cubes, triangular prisms, etc.

Typical nozzle plates 1720 include one or more openings for air flow and particles to pass through. Generally, lower stage nozzle plates 1720 have higher quantities of openings 1725 having smaller diameters than upper stage nozzle plates 1720. This allows for particles of different size ranges to be measured. Some embodiments include an alignment notch to allow the nozzle plate 1720 to be properly aligned with a corresponding impaction plate through the use of an alignment structure.

Figure 18:
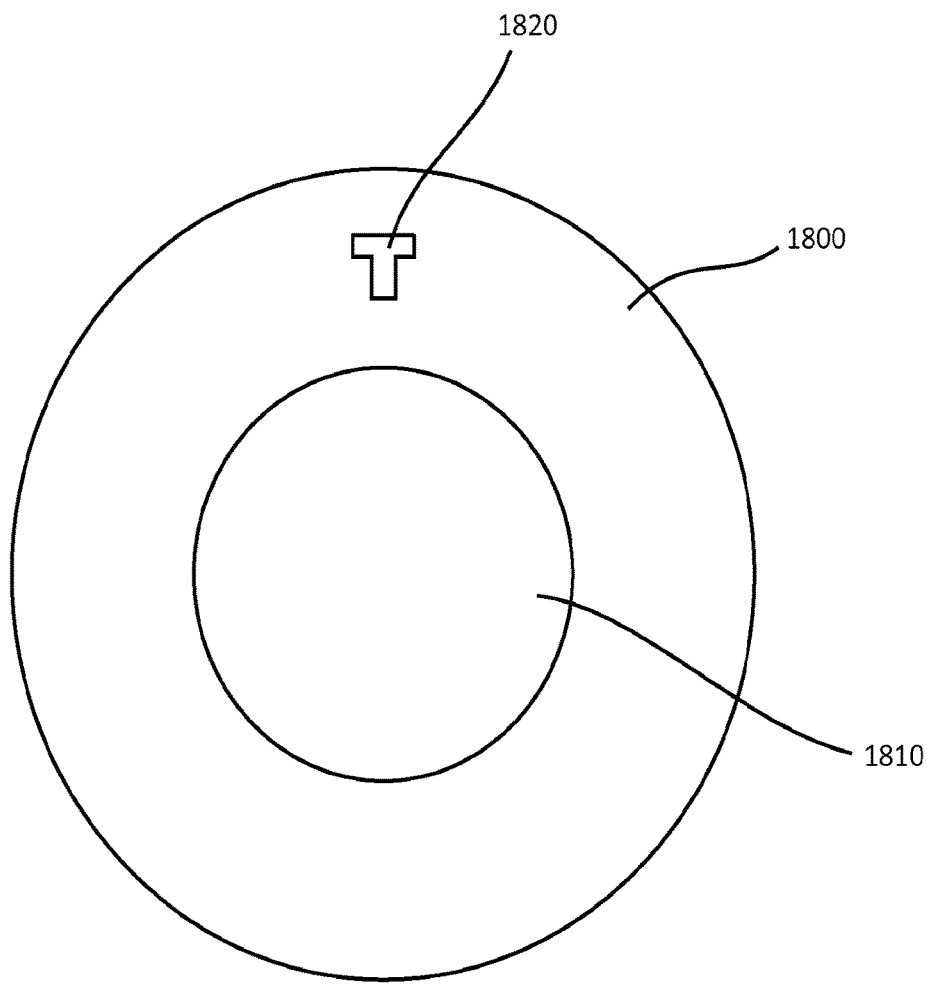
FIG. 18 shows the schematic view of a nozzle substrate for upper stages of a c existing or future technologies. This description should not be interpreted as implying any particular order or arrangement among or between various steps or elements except when the order of individual steps or arrangement of elements is explicitly described. Like numerals within the drawings and mentioned herein represent substantially identical structural elements. Each example is provided by way of explanation, and not as a limitation. For instance, features illustrated or described as part of one embodiment may be used on another embodiment to yield a further embodiment. Thus, it is intended that this disclosure includes modifications and variations.

For example, FIG. 18 depicts an upper stage nozzle plate 1800 having an opening 1810. Alignment notch 1820 allows for the nozzle plate 1800 to be properly aligned with a corresponding impaction plate through the use of an alignment structure 2200. FIG. 19 shows an example of a lower stage nozzle plate 1900 having a plurality of smaller openings 1910. Alignment notch 1920 allows for the nozzle plate 1900 to be properly aligned with a corresponding impaction plate through the use of an alignment structure 2200.

Typical impaction plates comprise one or more MEMS resonators, often in a large array. MEMS resonators can be of different sizes and sensitivity levels in different stages of impaction, allowing for a variety of particle sizes to be measured. In some embodiments, the resonators' electrical connections are terminated by pads at the edges of the substrate. These pads can have footprints compatible with plug-in micro-connectors to allow for easy access and replacement of resonator chips. Each MEMS resonator requires one electrical connection to deliver a DC bias current to the resonator. In some embodiments, this is achieved by sending a current to the resonators via the pads. An AC voltage for the oscillator can be induced on the same electrical connection. In some embodiments, the pads can have further interfaces for measuring and processing circuitry, as well as for data collection or a user interface connected to a display device. MEMS can initiate and maintain self-oscillation without the need for any external electronic amplification and therefore require only simple digital circuitry to measure and record the deposited mass on them.

MEMS resonators further require ground connections, which can be common among all resonators on the same impaction plate. In one embodiment, ground connections are placed on the impaction plate in such a manner as to isolate them from each other, allowing them to carry a 3-phase particulate sweeping signal. Some embodiments include an alignment notch properly align the impaction plate with a corresponding nozzle plate through the use of an alignment structure.

For example, FIG. 20 shows an upper stage impaction plate 2000 having resonators 2010. The MEMS resonators' 2010 electrical connections are terminated by pads 2020. Resonators 2010 further comprise ground connections 2030 alignment notch 2040 which allows for the impaction plate 2000 to be properly aligned with a corresponding nozzle plate through the use of an alignment structure 2200. FIG. 21 shows an example of a lower stage impaction plate 2100 having MEMS resonators 2110. The MEMS resonators' 2110 electrical connections are terminated by pads 2120 and have ground connections 2130. Alignment notch 2140 allows for the impaction plate 2100 to be properly aligned with a corresponding nozzle plate through the use of an alignment structure 2200.

Figure 22:
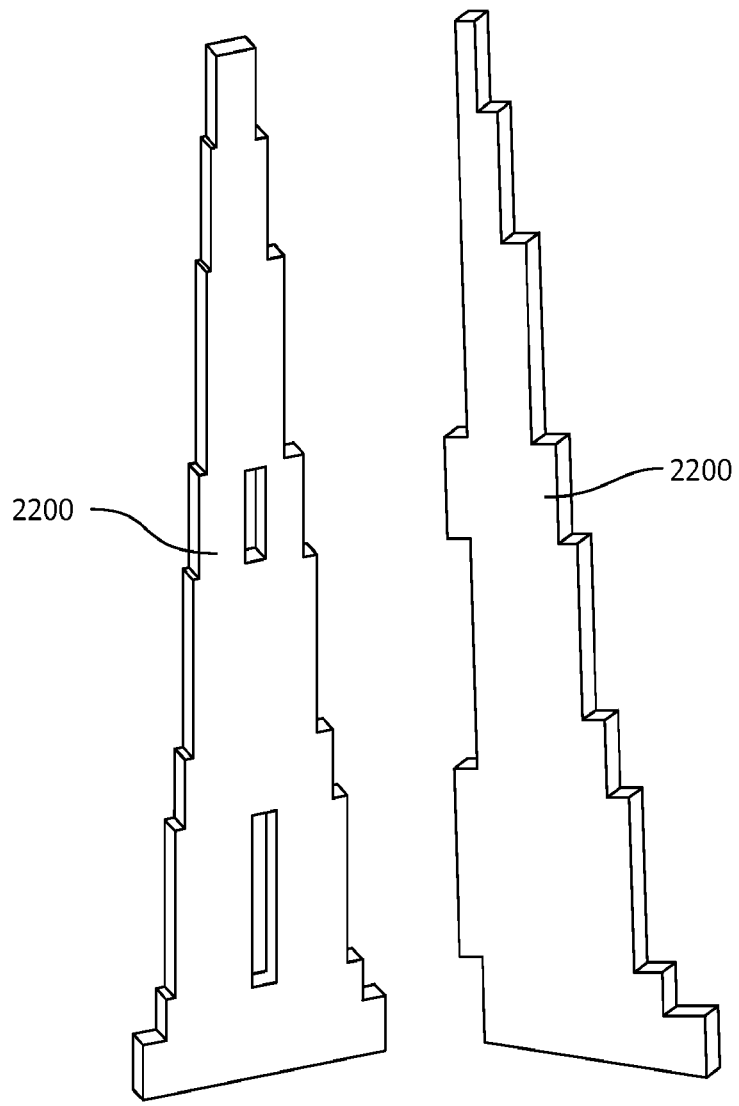

One embodiment of an alignment structure 2200 is shown in FIG. 22. Alignment structure 2200 can have a stepped size structure to allow for proper alignment and set up of nozzle plates and their corresponding impaction plates. Additional embodiments utilize a T-shaped cross-section to fix the alignment of the nozzle plates and impaction plates in their properly aligned positions.

Figure 23:
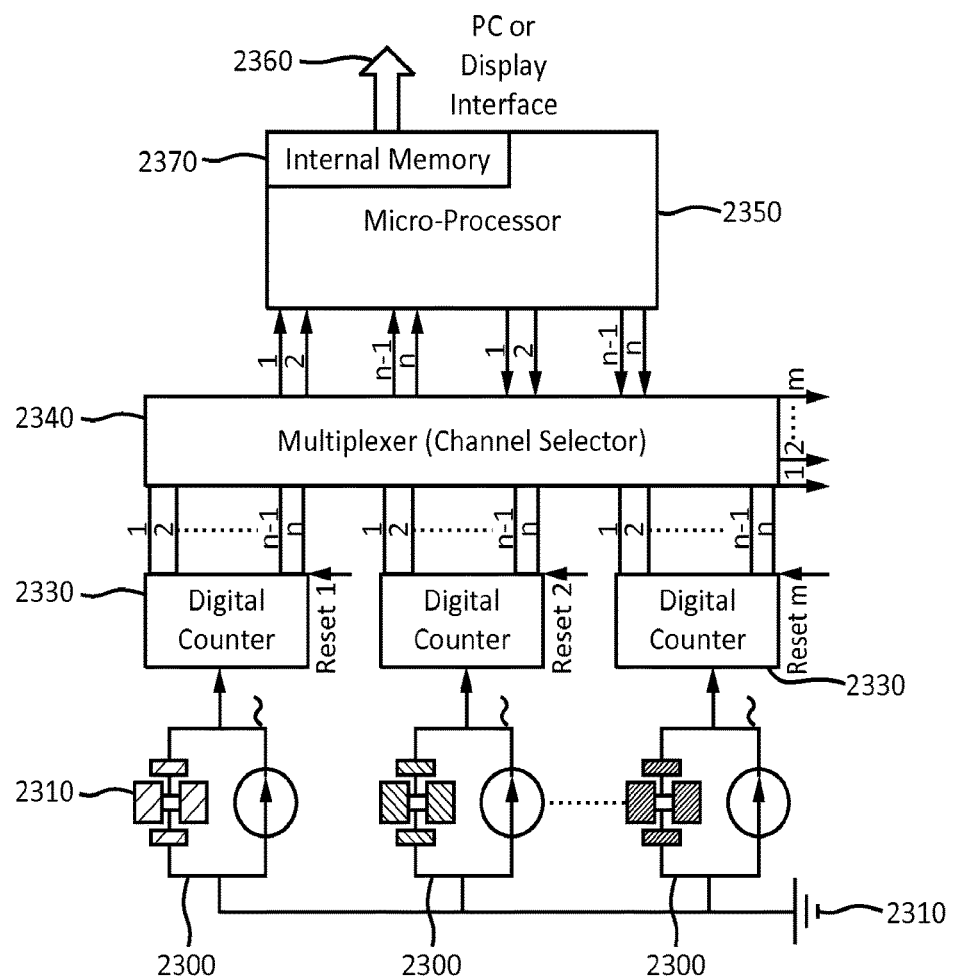

FIG. 23 shows the schematic view of the digital circuitry required for collecting the data from an array 2300 of self-sustained micromechanical resonators 2310. Each resonator 2310 in the array 2300 comprises a MEMS resonator 100 and a bias current source, and each MEMS resonator 100 is attached to ground 2320. To measure frequency of the resonators 2310, the output signal of each resonator 2310 is applied to the trigger input of a digital binary counter 2330. Frequency for all the resonators is counted simultaneously and the output of the digital binary counters 2330 is read one by one by a microprocessor 2350 through a multiplexor 2340. The microprocessor 2350 has to be programmed to time the readout of each digital binary counter 2330 precisely and send the "reset" command to each digital binary counter 2330 after reading its output. Readout interval in the order of one second is long enough to provide a high frequency measurement precision and short enough to allow detection of arrival of every single particle. Microprocessor 2360 continues this read and reset polling process for each digital counter 2330 one by one for every period. A period can range from 0.1 to 10 seconds depending on the particle concentrations in the air. Microprocessor 2350 then can send outputs to a PC or other display interface 2360. Some embodiments of the invention include internal memory 2370 for storage of the microprocessor outputs. Implementation of such readout circuitry for an instrument including tens of resonators will require the use of FPGAs to integrate all the digital components, including the microprocessor 2350 into one single chip.

Figure 24:
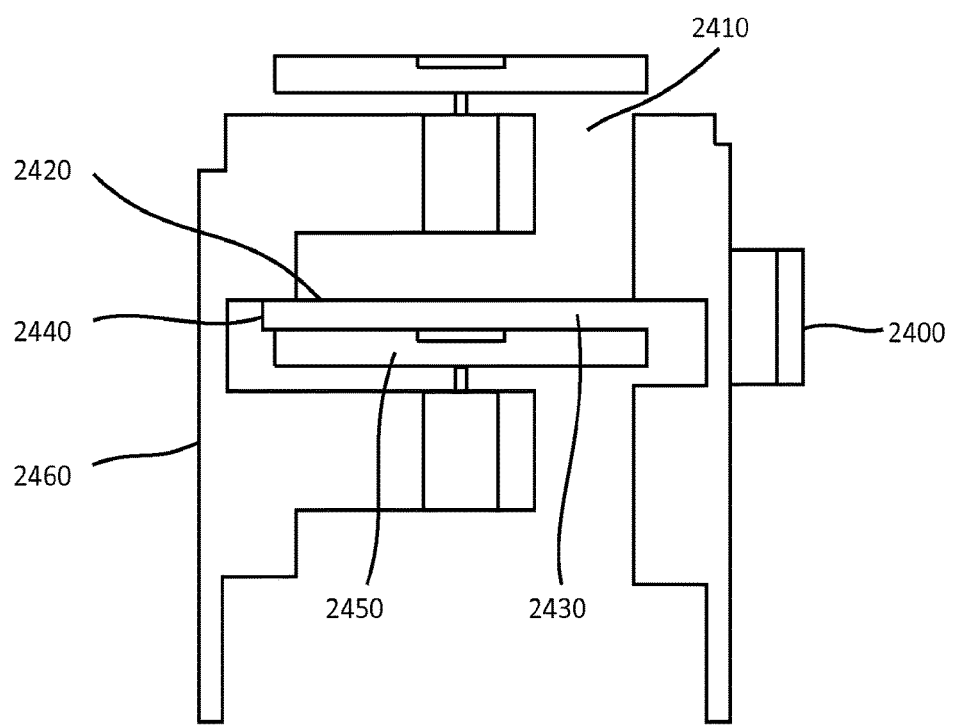

FIG. 24 shows an air input 2410 leading to a single impaction stage 2400. The impaction stage 2400 contains a nozzle plate 2420, which is perforated with at least one opening 2430. Air containing aerosol particles is accelerated in the openings 2430 in the nozzle plate 2420 and the particles larger than a cut-point 2440 are deposited by inertia onto an impaction plate 2450. The impaction plate 2450 contains MEMS resonators whose frequencies will shift as the particles are deposited. The impaction plate 2450 can be electrically coupled to an electric bus 2460. In some examples, the electrical bus can be connected to a processor, an FPGA, a memory device, a PC, and/or other display module. The transmission of frequency shifts of MEMS resonators via electric bus 2460 allow particle mass and concentration levels to be measured and reported in real-time.

For example, if particulate mass concentration of 50 $\mu g/m^3$ cited for Beijing is collected utilizing existing cascade impactor design on one impactor stage, it would be delivered to the impaction surface at the rate of 50 $\mu g/m^2 s$. A MEMS resonator of size 10 $\mu m \times 10$ $\mu m \times 2$ $\mu m$ integrated into the impaction plate would experience a measureable, fractional frequency shift of 10 ppm in 0.9 seconds. Distributing the same mass over 10 stages, assuming the same mass concentration in each size range, would lead to a response time of 9 seconds, showing that MEMS sensitivities are appropriate to rapid characterization of polluted environments and convenient characterizations of cleaner ones.

Figure 25:
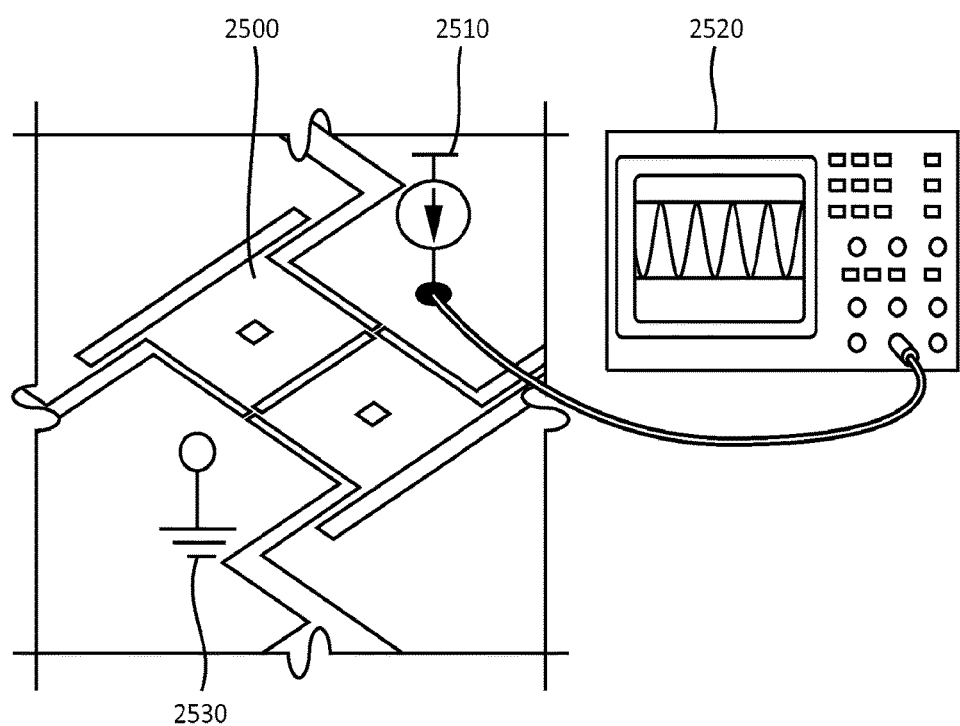

An electron micrograph of a 4.6 MHz dual-plate MEMS resonator 2500 capable of self-sustained oscillation is shown in FIG. 25. The MEMS resonator 2500 is activated by a direct current 2510 indicated by the current supply shown as a circle with an arrow in it. The MEMS resonator 2500 is connected to ground 2530. The oscillation of the MEMS resonator 2500 can be observed by oscilloscope 2520.

Figure 26:
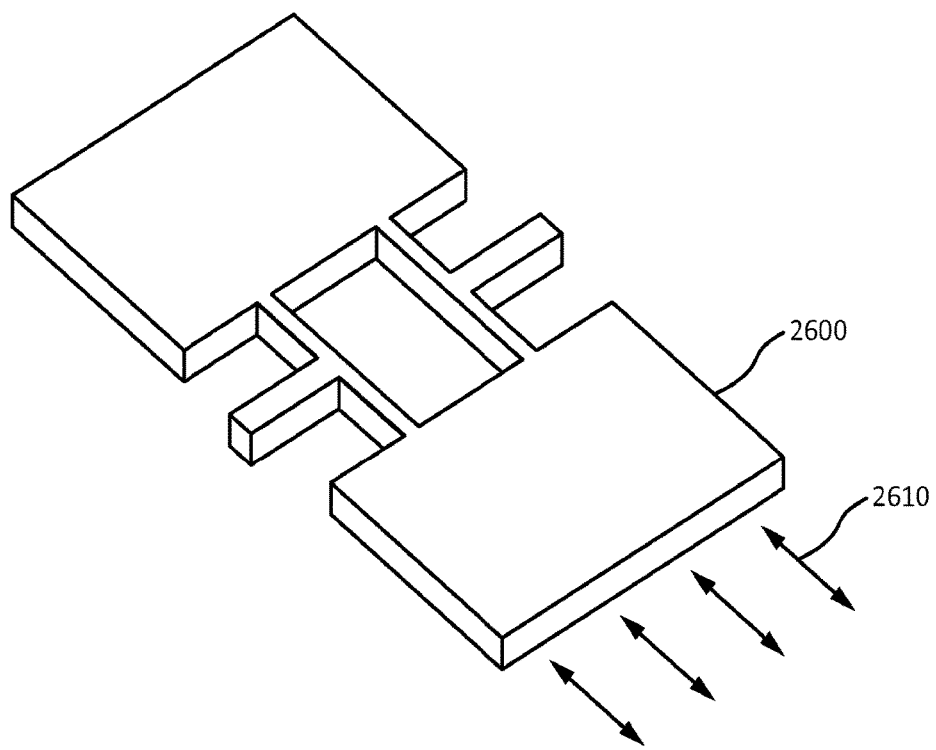

The finite element modal analysis results for a dual plate resonator showing its in-plane resonant mode is shown in FIG. 26. In this mode, the two symmetric masses (plates) resonate back and forth in opposite directions in response to the thermal excitation provided by driving an AC current through the point of attachment. The plates do not deform as the resonator vibrates and maintain a uniform vibration amplitude over their whole area. The direction of the oscillation of MEMS resonator 2600 is indicated by the arrows 2610.

Figure 27:
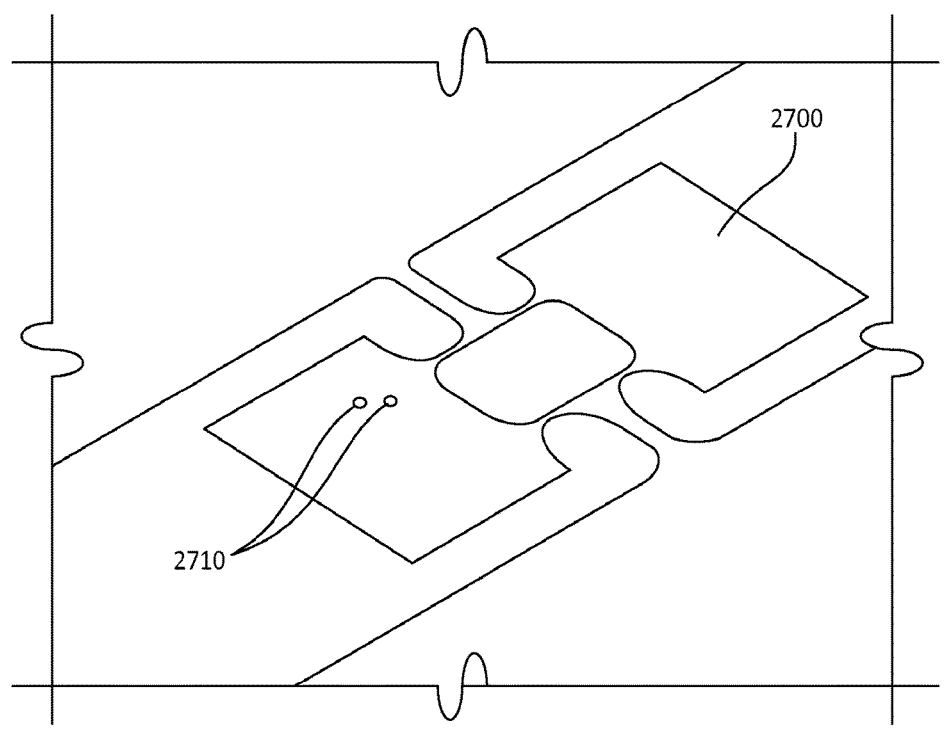
Figure 28:
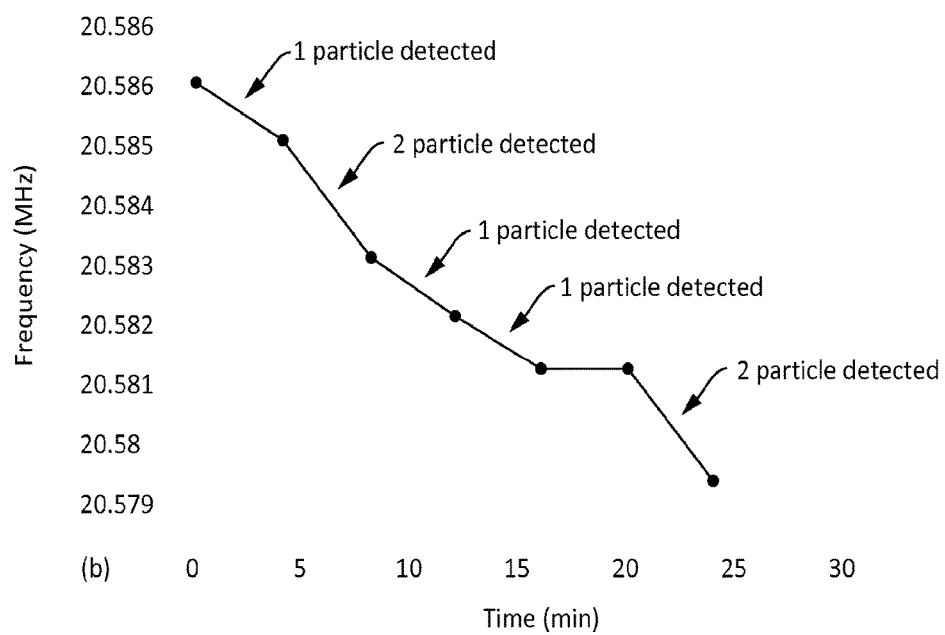
Figure 29:
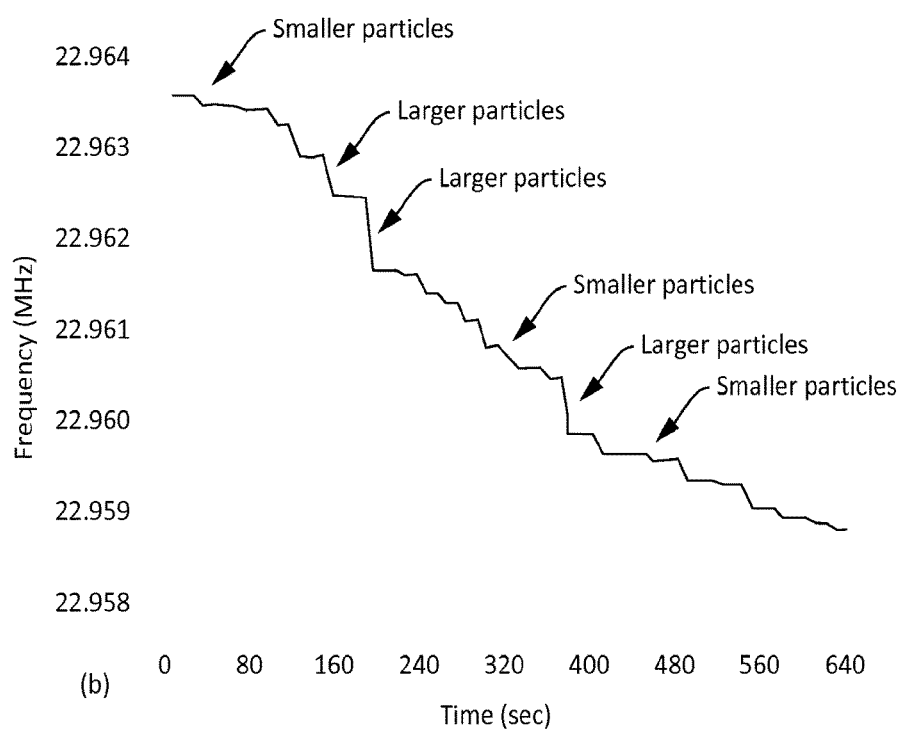
Figure 30:
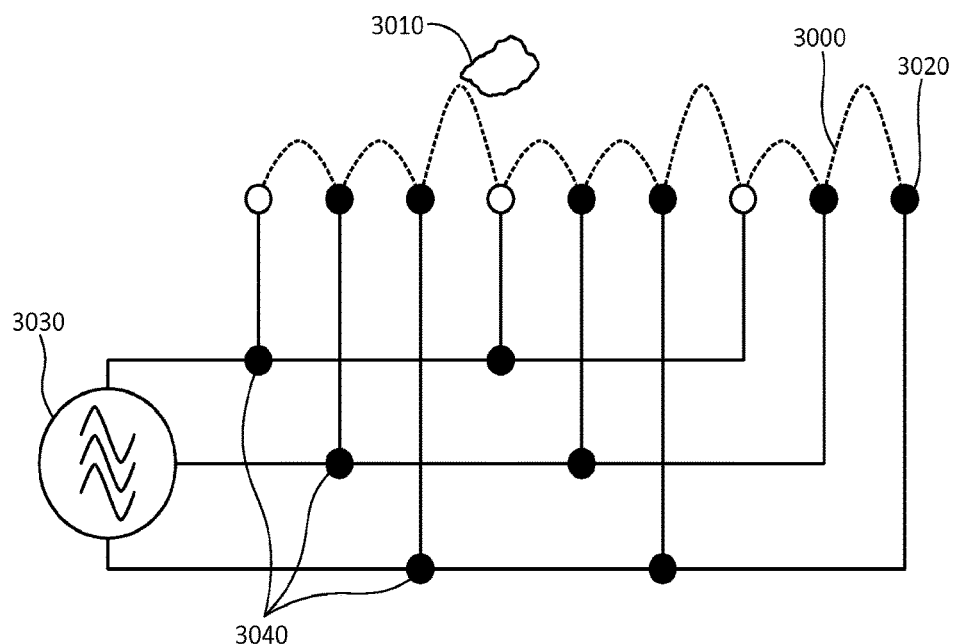
Figure 31:
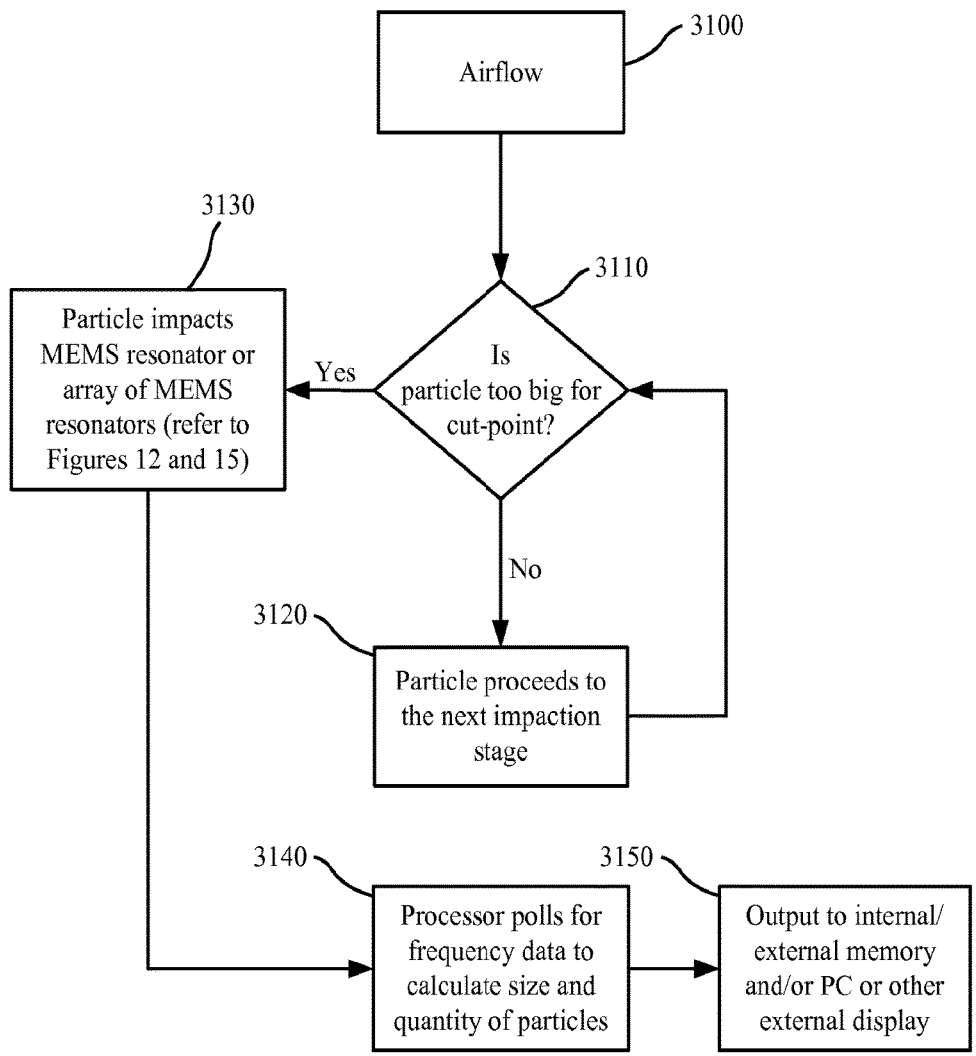
Figure 32:
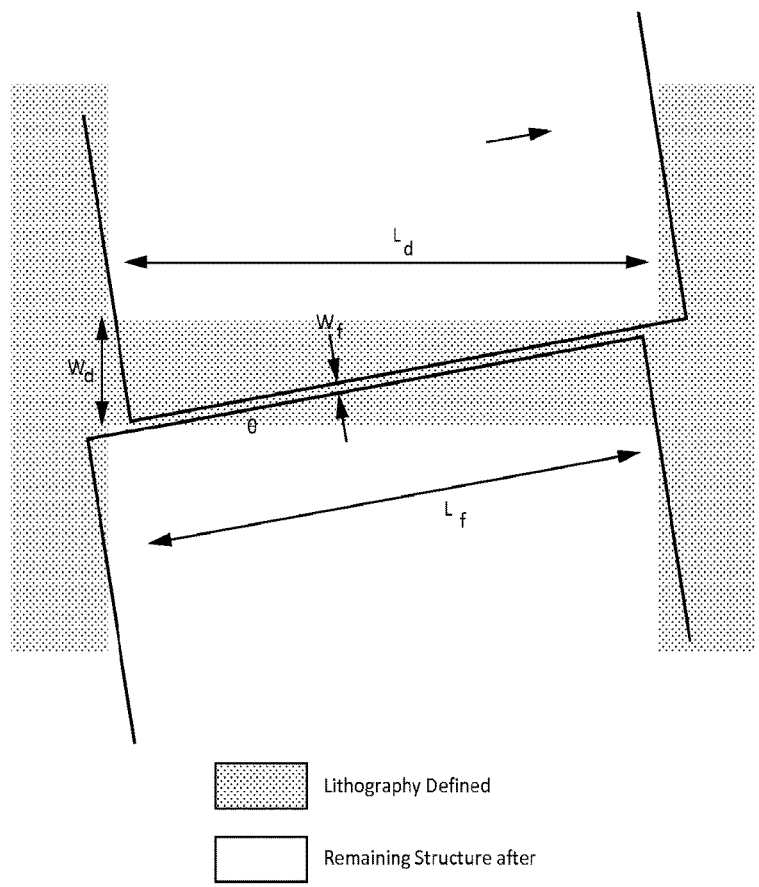

FIG. 27 shows an electron micrograph of a MEMS resonator 2700 having two symmetric masses resonating back and forth in opposite directions in response to the thermal excitation provided by driving an AC current through the points of attachment. The current causes fluctuating local heading and thermal expansion. If the actuation frequency is equal to the mechanical natural frequency of the structure, the vibration amplitude maximizes. The device was fabricated on a SOI substrate with device layer thickness of 3 µm using a single photolithography step followed by silicon and oxide etching to form the structure and undercut. The MEMS resonator 2700 has been loaded with monodisperse aerosol particles 2710 having a diameter of 1 micron. The resulting change in resonant frequency of the MEMS resonator 2700 due to the particle deposit is shown in the graph in FIG. 28. The frequency to mass sensitivity of the resonator has been measured to be 1.6 kHz/pg, which is in good agreement with theoretical calculations based on the effective mass of the resonator. This device detected the arrival and measured the mass of each particle.

Given particles that are roughly the same size, corresponding changes of frequency result in slopes proportional to the number of particles detected during a given interval.

FIG. 29 shows a graph of shift in measured resonance peak towards lower frequencies for a dual plate resonator exposed to a flow of regular air in a lab for 640 seconds. In this experiment frequency measurements are performed in short intervals to decrease the probability of more than one particle reaching the resonator during each interval. Therefore, the frequency shift during each interval provides information on whether or not a particle has arrived and if so, how large that specific particle is. Frequency shifts caused by particles weighing as little as 15 fg (~200 nm diameter assuming a density of 3 $g/cm^3$) are measurable for this resonator. Micro and nanoscale airborne particle were deposited on the resonator. Over the exposure period, an overall frequency shift of −4.7 KHz occurred, indicating 205 ppm. The frequency shift during each interval allows for the determination of the mass of the deposited particles during each interval, as particles of increasing mass result in more substantial changes in frequency.

Experiments have shown that TPRs, which include MEMS resonators 100, typically stop working after collecting particle mass in the order of 1-3% of the mass of the resonator. While this level is sufficient to collect of large number of particles for a statistically valid distribution analysis, especially through the use of an array of resonators, it would still be highly beneficial to increase the resonator lifetimes to minimize the cost and effort associated with resonator chip replacements. Accordingly, one embodiment of the present invention shown in FIG. 30 utilizes a particle sweep signal 3000 to remove the deposited particles 3010 from the resonator surfaces 3020. This enhances the overall resonator lifetime and increases the sensitivity of the resonators. A particle sweeping signal 3000 is an electrodynamic process where a series of parallel electrodes 3040 are connected to a multi-phase AC source 3030. The AC source 3030 generates a traveling wave that carries dust particles 3010. Electrodynamic sweeping signals can be used to remove the particulate from resonators, prolonging the life of the resonators. Successful implementation of the electrodynamic particle sweeps will allow multiple to infinite measurement cycles before the resonator chips have to be replaced.

FIG. 30 shows a three phase electron curtain 3000 sweeping a charged particle 3010 in the direction of the resulting wave. This technique has been shown to lift and transport charged and uncharged particles using electrostatic and dielectrophoretic forces. Although the forces responsible for the levitation of the particles are highly dependent on their charge, uncharged particles can ultimately be removed from the curtain as well. It has been well documented that polarizable particles can be levitated using these techniques. Since many larger neutral particles contain nearly equal amounts of positive and negative charges on their surface, these particles possess an extrinsic electric dipole moment. If this dipole moment is exposed to a spatially non-uniform electric field, the particles will experience a force. Likewise, particles with intrinsic electric dipole moment s or containing polar materials like water will also experience a force. Experiments have shown successful removal of 50-75 μm dust particles from solar panel surfaces. The line spacings in the millimeter range and relatively large particles sizes in such experiments necessitate large voltage amplitudes as high as 1 kV at 10 Hz. Although such high voltages can be generated from lower battery voltages using relatively simple electronics (charge pumps), microscale electrodynamic shields integrated on microsensor substrates require orders of magnitude lower voltages to operate. Ground connections for different resonators on impaction plates are isolated from each other allowing them to carry a 3-phase particulate sweeping signal. To avoid interferences, the oscillators are to be turned off during a particle sweep step.

FIG. 31 shows a flow chart of the operation of one example of a MEMS aerosol impactor. Airflow is introduced at block 3100 to the impactor utilizing a device such as a pump, to create a low pressure environment within the impactor. Aerosol particles enter the impactor and one of two processes occurs. The particle either fits through the cut-point or is trapped in the current impactor stage at block 3110. If the particle fits through the cut-point it proceeds to the next impaction stage at block 3120. Once a particle reaches an impaction stage where the cut-point is too small to pass through, the particle impacts a MEMS resonator or an array of MEMS resonators on an impaction plate at block 3130. These MEMS resonators 100 function as described above in descriptions of FIGS. 12 and 15. After being impacted by particles at block 3130, the frequency of MEMS resonators 100 is changed. A processor coupled to the MEMS resonators 100 via a bus polls the MEMS resonators 100 for their frequencies, and calculates the size and quantity of the particles present at block 3140. This data may be stored in internal or external memory, as well as sent to a PC or other external display at block 3150.

FIG. 32 shows a self-aligned nanofabrication technique that can be utilized to manufacture smaller MEMS resonators 100. Mass sensitivity as high as 1.6 kHz/pg has been demonstrated for 3 μm thick resonators. Frequency shifts as small as a few Hz are likely easily measureable by smaller resonators. Detection of individual particles with mass as small as 8 fg, equivalent to ~200 nm diameter, has been demonstrated using such resonators. Individual particles with diameters as small as 50 nm could be detected and their mass measured with resonators dimensions in the nanoscale. Shrinking the resonator vertical dimensions (thickness) can be accomplished by fabricating the resonator on SOI substrates with a thinner device layer. In order to shrink the lateral dimensions deep submicron actuator beam widths must be utilized. This can be achieved by ebeam lithography, although this does not provide a commercially viable solution. A self-aligned nanofabrication technique which utilizes the crystalline structure of silicone to provide the ultimate high-precision alignment and size control to define nanoscale features.

The technique is based on anisotropic wet etching of silicon in alkaline solutions that can provide extremely smooth surfaces and well-defined features with atomic level precision. Inducing a slight rotational misalignment between the photo-lithography defined patterns and the crystal orientation of the silicon substrate results in the undercutting of the mask layer and leaving behind much smaller feature sizes after etching, provided that the etch time is long enough. The main advantage of such undercut over the undercut resulting from isotropic wet or dry etch processes is its self-control and relative independence from the rate and timing of the etch process. The first plane in the sidewall that is fully covered by the mask on top acts as a strong etch-stop during the undercut. The size of the final structure is defined by the angle between the initial pattern and the appropriate crystalline orientation (110 direction in the case of 100 silicon substrate) and the size of the lithographically defined initial pattern $W_f = W_d \cos\Theta - L_d \sin\Theta$, where $L_d$ and $W_d$ are the initially defined dimensions on the etch mask, $L_f$ and $W_f$ are the dimensions of the resulting structure after a long enough etch, and $\Theta$ is the angle between the initial pattern and the crystalline orientation. This technique will be refined and utilized to fabricate resonators with plate area smaller than 10 μm² and sub-100 nm actuator width.

As sensitive mass sensors, micromechanical resonators can potentially open up a wide range of new opportunities in biomedical and chemical sensing applications leading to more compact low cost instruments with real-time sensing capabilities. Implemented into small impactors, MEMS resonators can provide real-time monitoring of concentrations of hazardous aerosol particles. For example, air quality conditions in mining operations can be monitored, providing much safer environments for mine workers. Individuals encountering poor air quality can wear a MEMS impactor to ensure that the individual is not exposed to hazardous particulate levels. Further applications include monitoring atmospheric conditions, as well as ensuring that laboratories are sufficiently sterile. Clean room and micro/nanofabrication labs often maintain very strict air purity requirements which can be actively monitored by MEMS impactors.

Many biosensing applications require detection and measurement of certain molecules in a liquid solution. MEMS resonators and impactors can be designed to work with fluids other than air. For example, MEMS impactors can be configured to measure particulate in drinking water or the purity of non-air gases.

One of the major factors limiting the minimum detectable frequency shift in a silicon resonator is the temperature drift of the resonator. Frequency shifts as low as 1 ppm can be easily measured for the proposed silicon resonators. However, uncompensated silicon resonators have temperature coefficient of frequency as large as −40 ppm/° C. Assuming a temperature swing of up to 10° C. during a single measurement, this translates into an overall frequency uncertainty of 400 ppm. This limits the minimum detectable mass by 400×. The temperature drift of frequency can be highly suppressed using high phosphorous doping concentrations in the silicon resonators. For example, temperature stability as high as 0.05 ppm/° C. for high frequency thermally actuated resonators can be achieved. This would limit the frequency uncertainty resulting from a 10° C. temperature swing to 0.5 ppm allowing frequency measurement accuracy in the 1 ppm range.

Another capability that can be integrated within MEMS impactors is the real-time analysis of water and organic content of the collected particles. Water and organic compounds contribute significantly to the mass, optical and hygroscopic properties of ambient aerosol particles. The change of particle size with humidity strongly affects amount of light that the particles scatter. Organic species also impact their refractive index. Both the hygroscopic behavior of particles and their organic compositions are important in determining their effectiveness as cloud condensation nuclei. Uncertainties concerning the abundance, optical and hygroscopic properties of aerosol particles make efforts to quantify the direct and indirect effects of particles on climate more difficult. This also makes climate sensitivity and predicting future climates more uncertain.

The spatial and temporal inhomogeneity of the atmospheric aerosol means that the global distribution cannot be accurately characterized based on a small number of measurements in limited locations or in intensive studies. The water and organic contents of airborne particles are often studied with Tandem Differential Mobility Analyzers (TDMA) and thermal-desorption mass spectrometry. The TDMA and the mass spectrometer techniques involve expensive, heavy and large instruments. The instruments that the proposed technology promises to develop will be much smaller and cheaper and therefore able to be more widely deployed. These instruments will provide information on the fraction of aerosol mass due to water and the mass of volatile organics. This information will be available for total aerosol mass and for size fractionated samples and can be used to predict humidity dependent optical properties and CCN spectra.

The ambient aerosol will be characterized using the proposed micromachined cascade impactors with integrated MEMS resonant mass sensors which report accumulated mass in size fractions as a function of time. The water and volatile organic content can be determined in one of two ways. The first way is to heat the collected sample and watch the mass change as a function of temperature. For example, this could simply be performed by passing a large bias current through the resonators causing excessive ohmic heating. The second way is to operate parallel cascade impactors. One would measure the ambient aerosol; the others would measure samples that are pretreated by heating or drying. The differences permit the mass of water or volatile organics to be determined. The conditioning with specified humidity or temperature changes will be much easier to realize since the sample flow into the impactors is quite small.

The foregoing is provided for purposes of illustrating, explaining, and describing embodiments of the present invention. Further modifications and adaptations to these embodiments will be apparent to those skilled in the art and may be made without departing from the scope or spirit of the invention. Different arrangements of the components depicted in the drawings or described above, as well as components and steps not shown or described are possible. Similarly, some features and subcombinations are useful and may be employed without reference to other features and subcombinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications can be made without departing from the scope of the claims below.

What is claimed is:

1. A particle impactor comprising:
 a housing;
 a nozzle disposed within the housing that includes an aperture to allow for the passage of air through the housing; and
 a microelectromechanical systems (MEMS) resonator positioned within the housing to capture particles within the air flowing through the housing, wherein the particles are within a predetermined size group, and wherein the MEMS resonator has a resonant frequency that shifts when a particle impacts a portion of the resonator,
 wherein:
  the nozzle is one of a plurality of nozzles;
  the MEMS resonator is one of a plurality of MEMS resonators,
  each nozzle is aligned with a corresponding MEMS resonator, wherein each successive nozzle is configured to allow particles with different predetermined size groups to flow through the housing, and each successive MEMS resonator is configured to be sensitive to frequency shifts to detect the presence of different sized particles.

2. The particle impactor as in claim 1, wherein the plurality of MEMS resonators are disposed on an impactor surface positioned below the corresponding nozzle.

3. The particle impactor as in claim 1, wherein the particle impactor is powered by a battery.

4. The particle impactor as in claim 1, wherein the MEMS resonators are less than or equal to 400 µm2 in area.

5. The particle impactor as in claim 1, wherein the MEMS resonators are less than or equal to 10 µm2 in area.

6. The particle impactor as in claim 1, wherein the particle impactor has a volume less than or equal to 40 cm$^3$.

7. The particle impactor as in claim 1, wherein the particle impactor has a volume less than or equal to 10 cm$^3$.

8. The particle impactor as in claim 1, wherein each MEMS resonator comprises two masses coupled with at least one beam, and two pads electrically coupled with the beam, wherein the masses resonate with a fixed frequency when a constant current runs through the beam.

9. The particle impactor as in claim 8, wherein each MEMS resonator further comprises a second beam coupled with each of the two masses.

10. The particle impactor as in claim 1, wherein each MEMS resonator comprises doped silicon.

11. The particle impactor as in claim 1, wherein each MEMS resonator is connected to an electrical bus, a processor, and a memory device, wherein the processor is configured to convert frequency shifts to particle mass or particle concentration data.

12. The particle impactor as in claim 11, wherein the processor is configured to indicate mass or particle concentration data in real-time.

13. The particle impactor as in claim 1, wherein each MEMS resonator comprises:
a disk;
a first beam coupled with the disk;
a second beam coupled with the disk;
a first pad electrically coupled with the first beam; and
a second pad electrically coupled with the second beam;
wherein either or both a direct bias current and an alternating bias current flows through the first beam and the second beam.

14. A method for measuring particulate concentration, comprising:
flowing air through a plurality of nozzles disposed within the housing which each include an aperture to allow for the passage of air through the housing;
filtering aerosol particles within the air;
measuring a frequency shift of a plurality of microelectromechanical systems (MEMS) resonators positioned within the housing to capture particles within the air flowing through the housing as the aerosol particles impact the MEMS resonators; and
determining the mass or concentration of aerosol particles in a size group using the frequency shift,
wherein:
each nozzle is aligned with a corresponding MEMS resonator, wherein each successive nozzle is configured to allow particles with different predetermined size groups to flow through the housing, and
each successive MEMS resonator is configured to be sensitive to frequency shifts to detect the presence of different sized particles.

15. The method as in claim 14, further comprising indicating particulate mass or concentration levels in real-time.

16. A particle impactor comprising:
a housing having a volume less than or equal to 10 cm$^3$;
a nozzle disposed within the housing, wherein the nozzle comprises a plurality of micromachined apertures to allow for the passage of air through the housing; and
a micro-electromechanical resonator positioned within the housing near the nozzle to capture particles within the air flowing through the housing, wherein the particles are within a predetermined size group, and the micro-electromechanical has an area less than or equal to 100 µm2, and wherein the micro-electromechanical resonator has a resonant frequency that shifts when a particle impacts a portion of the micro-electromechanical resonator,
wherein the micro-electromechanical resonator comprises a plurality of isolated ground connections configured to generate an electrodynamic particle sweep.

17. The particle impactor as in claim 16, wherein:
the nozzle is one of a plurality of nozzles;
the micro-electromechanical resonator is one of a plurality of micro-electromechanical resonators,
each nozzle is aligned with a corresponding micro-electromechanical resonator, wherein the plurality of micromachined apertures of each successive nozzle are configured to allow particles with different predetermined size groups to flow through the housing, and
each successive micro-electromechanical resonator is configured to be sensitive to frequency shifts to detect the presence of different sized particles.

18. The particle impactor as in claim 16, wherein the micro-electromechanical resonator is one of a plurality of micro-electromechanical resonators disposed on an impactor surface positioned below the nozzle.

* * * * *